(12) United States Patent
Sun et al.

(10) Patent No.: US 7,410,990 B2
(45) Date of Patent: Aug. 12, 2008

(54) HETEROCYCLIC COMPOUNDS

(75) Inventors: Lijun Sun, Harvard, MA (US);
Mitsunori Ono, Lexington, MA (US);
Yumiko Wada, Billerica, MA (US);
Weiwen Ying, Ayer, MA (US); Teresa Przewloka, Tewksbury, MA (US); Elena Kostik, Arlington, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 11/542,963

(22) Filed: Oct. 3, 2006

(65) Prior Publication Data

US 2007/0027151 A1 Feb. 1, 2007

Related U.S. Application Data

(63) Continuation of application No. 10/686,505, filed on Oct. 14, 2003, now Pat. No. 7,122,665.

(60) Provisional application No. 60/418,984, filed on Oct. 15, 2002.

(51) Int. Cl.
*A61K 31/4184* (2006.01)
*A61K 31/5377* (2006.01)
*C07D 265/30* (2006.01)
*C07D 235/30* (2006.01)

(52) U.S. Cl. .............. 514/395; 514/232.5; 544/80; 548/304.4; 548/304.7

(58) Field of Classification Search .............. 544/139; 548/304.7, 304.4; 514/395
See application file for complete search history.

(56) References Cited

U.S. PATENT DOCUMENTS

| | | | |
|---|---|---|---|
| 4,459,296 | A | 7/1984 | Ancher et al. |
| 4,946,843 | A | 8/1990 | Janssens et al. |
| 5,864,037 | A | 1/1999 | Chasin et al. |
| 6,384,032 | B1 | 5/2002 | Ono et al. |
| 6,680,733 | B2 | 12/2003 | Sun et al. |
| 6,680,315 | B2 | 1/2004 | Ono et al. |
| 6,693,097 | B2 | 2/2004 | Ono et al. |
| 7,045,517 | B2 | 3/2004 | Ono et al. |
| 7,067,514 | B2 | 3/2004 | Ono et al. |
| 6,858,606 | B2 | 2/2005 | Sun et al. |
| 6,958,332 | B2 | 10/2005 | Sun et al. |
| 7,122,665 | B2 * | 10/2006 | Sun et al. .................. 544/118 |
| 2005/0250787 | A1 | 11/2005 | Sun et al. |

2006/0025409 A1 2/2006 Ono et al.

FOREIGN PATENT DOCUMENTS

| WO | WO 9926932 A1 * | 6/1999 |
|---|---|---|
| WO | WO-00/78757 A1 | 12/2000 |
| WO | WO-2005/000404 A1 | 1/2005 |

OTHER PUBLICATIONS

Barrie et al. (Clinical and Applied Immunology Reviews 2005, 5, 225-240).*
Comabella et al. (J. Clin. Invest. 1998, 102(4), 671-678).*
Schmidt et al. (Pathobiology 2002-03, 70, 177-183).*
Adorini, L. (Nature Genetics 2001, 27, 131-132).*

* cited by examiner

*Primary Examiner*—Rebecca L Anderson
*Assistant Examiner*—Jason M Nolan
(74) *Attorney, Agent, or Firm*—Edwards Angell Palmer & Dodge LLP; Jeffrey D. Hsi; Mark D. Russett

(57) ABSTRACT

This invention features a compound of formula (I):

(I)

[Chemical structure diagram]

$R_1$ is aryl or heteroaryl; each of $R_2$ and $R_4$, independently, is H, halogen, CN, alkyl, $OR^a$, or $NR^aR^b$; $R_3$ is H, halogen, CN, alkyl, alkenyl, alkynyl, aryl, heteroaryl, cyclyl, heterocyclyl, $OR^a$, $OC(O)R^a$, $OC(O)NR^aR^b$, $NR^aR^b$, $NR^aC(O)R^b$, $NR^aS(O)R^bNR^aS(O)_2R^b$, $NR^aC(O)NR^bR^c$, $NR^aC(S)NR^bR^c$, $NR^aC(NR^b)NR^aR^d$, $NR^aC(O)OR^b$, $S(O)NR^aR^b$, $S(O)_2NR^aR^b$, $S(O)R^a$, $S(O)_2R^a$, $C(O)R^a$, $C(O)OR^a$, or $C(O)NR^aR^b$; $R_5$ is H or alkyl; n is 0, 1, 2, 3, 4, 5, or 6; A is O, S, S(O), $S(O)_2$, or $NR^e$; B is N or $CR^f$; X is O, S, S(O), $S(O)_2$, $NR^e$, or C(O); Y is a covalent bond, C(O), C=$NR^a$, O, S, S(O), $S(O)_2$, or $NR^e$; Z is N or CH; each of U and V, independently, is N or CR; and W is O, S, or $NR^e$; in which each of $R^a$, $R^b$, $R^c$, and $R^d$, independently, is H, alkyl, aryl, heteroaryl, cyclyl, or heterocyclyl; $R^e$ is H, alkyl, aryl, acyl, or sufonyl; and $R^f$ is H, alkyl, aryl, acyl, sulfonyl, alkoxyl, amino, ester, amide, CN, or halogen. The compound is useful for treating an interleukin-12 overproduction-related disorder.

21 Claims, No Drawings

HETEROCYCLIC COMPOUNDS

CROSS REFERENCE TO RELATED APPLICATIONS

This application is a continuation of U.S. patent application Ser. No. 10/686,505, filed Oct. 14, 2003, now U.S. Pat. No. 7,122,665, which claims the benefit of U.S. Provisional Application No. 60/418,984, filed Oct. 15, 2002. The contents of these applications are hereby incorporated by reference.

BACKGROUND

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Overproduction of IL-12 causes excessive Th1 responses, and may result in inflammatory disorders, such as insulin-dependent diabetes mellitus, multiple sclerosis, rheumatoid arthritis, psoriasis, Crohn's disease, or sepsis. See, e.g., Gately et al. (1998) *Annu Rev Immunol.* 16: 495; and Abbas et al. (1996) *Nature* 383: 787. Thus, inhibiting IL-12 overproduction is an approach to treat the just-mentioned diseases. Trembleau et al. (1995) *Immmunol. Today* 16: 383; and Adorini et al. (1997) *Chem. Immunol.* 68: 175. For example, overproduction of IL-12 and the resultarnt excessive Th1 type responses can be suppressed by modulating IL-12 production. A compound that down-regulates IL-12 production can be used for treating inflammatory diseases. Ma et al. (1998) *Eur Cytokine Netw* 9: 54.

SUMMARY

The present invention is based, in part, on the discovery of novel compounds, which are capable of modulating IL-12 production.

In one aspect, this invention features a compound of formula (I) that contains an aromatic bicyclic ring:

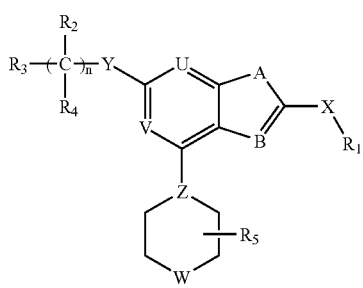

(I)

$R_1$ is aryl or heteroaryl; each of $R_2$ and $R_4$, independently, is H, halogen, CN, alkyl, $OR^a$, or $NR^aR^b$; $R_3$ is H, halogen, CN, alkyl, alkenyl, alkynyl, aryl, heteroaryl, cyclyl, heterocyclyl, $OR^a$, $OC(O)R^a$, $OC(O)NR^aR^b$, $NR^aR^b$, $NR^aC(O)R^b$, $NR^aS(O)R^b$, $NR^aS(O)_2R^b$, $NR^aC(O)NR^bR^c$, $NR^aC(S)NR^bR^c$, $NR^aC(NR^b)NR^cR^d$, $NR^aC(O)OR^b$, $S(O)NR^aR^b$, $S(O)_2NR^aR^b$, $S(O)R^a$, $S(O)_2R^a$, $C(O)R^a$, $C(O)OR^a$, or $C(O)N$-$R^aR^b$; $R_5$ is H or alkyl; n is 0, 1, 2, 3, 4, 5, or 6; A is O, S, S(O), $S(O)_2$, or $NR^e$; B is N or $CR^f$; X is O, S, S(O), $S(O)_2$, $NR^e$, or C(O); Y is a covalent bond, C(O), C=$NR^a$, O, S, S(O), $S(O)_2$, or $NR^e$; Z is N or CH; each of U and V, independently, is N or CR; and W is O, S, or $NR^e$; in which each of $R^a$, $R^b$, $R^c$, and $R^d$, independently, is H, alkyl, aryl, heteroaryl, cyclyl, or heterocyclyl; $R^e$ is H, alkyl, aryl, acyl, or sufonyl; and $R^f$ is H, alkyl, aryl, acyl, sulfonyl, alkoxyl, amino, ester, amide, CN, or halogen; and provided that if each of U and V is N, Y is a covalent bond, n is 0, then $R_3$ is H, CN, alkyl, alkenyl, alkynyl, aryl, heteroaryl, cyclyl, $OR^a$, $OC(O)R^a$, $OC(O)NR^aR^b$, $NR^aR^b$, $NR^aC(O)R^b$, $NR^aS(O)R^b$, $NR^aS(O)_2R^b$, $NR^aC(O)NR^bR^c$, $NR^aC(S)NR^bR^c$, $NR^aC(NR^b)NR^cR^d$, $NR^aC(O)OR^b$, $S(O)NR^aR^b$, $S(O)_2NR^aR^b$, $S(O)R^a$, $S(O)_2R^a$, $C(O)R^a$, $C(O)OR^a$, or $C(O)NR^aR^b$. Note that the left atom shown in any substituted group described above is closest to the aromatic bicyclic ring. Also note that when there are more than one $R^a$—containing substituted groups in a compound of formula (I), the $R^a$ moieties can be the same or different. The same rule applies to other similar situations.

Referring to the just-described compounds, a subset of these compounds is featured by that A is $NR^e$, and B is N. Another subset of the compounds are those wherein Z is N and W is O; or X is $NR^e$.

Further another subset of the compounds are those wherein each of U and V is N. In these compounds, A can be $NR^e$, B can be N, Y can be $NR^e$ or O, Z can be N, W can be O, $R_1$ can be aryl, and $R_3$ can be halogen, CN, alkyl, aryl, hetereoaryl, $OR^a$, $OC(O)R^a$, $NR^aNR^b$, $NR^aC(O)R^b$, $C(O)OR^a$, or $C(O)NR^aR^b$. In some embodiments, $R_3$ is aryl, heteroaryl (e.g., pyridinyl, triazolyl, tetrazolyl, pyrimidinyl, thiazolyl, indolyl, or indolizinyl), aryloxyl, or hetereoaryloxyl. In some other embodiments, $R_1$ is

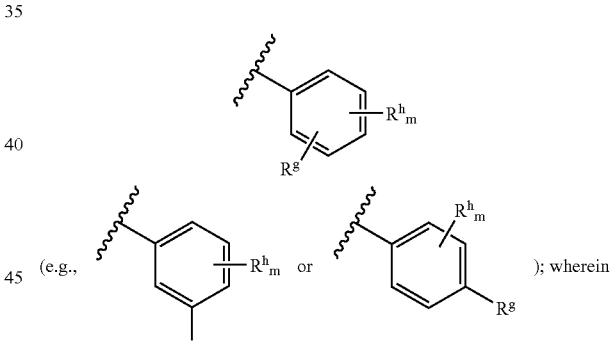

$R^g$ is H, halogen, CN, alkyl, or alkoxyl; $R^h$ is halogen (F, Cl, Br, or I), CN, hydroxyl, amino, alkyl (e.g., Me, Et, Pr, or i-Pr), aryl, heteroaryl, alkoxyl (e.g., OMe or OEt), aryloxyl, hetereoaryloxyl, acyl (e.g., $C(O)CH_3$), alkoxycarbonyl (e.g., $C(O)OCH_3$), alkylcarbonoxyl (e.g., $OC(O)CH_3$), mono- or dialkylaminocarbonyl (e.g., $NC(O(CH_3)_2)$), amidinyl (e.g., $C(NH)NH_2$), ureayl (e.g., $NHC(O)NH_2$), guanadinyl (e.g., $NHC(NH)NH_2$), sulfonyl (e.g., $SO_2CH_3$), or sufonamidyl (e.g., $SO_2NH_2$); and m is 0, 1, 2, 3, or 4.

Alkyl, alkenyl, alkynyl, aryl, heteroaryl, cyclyl, and heterocyclyl mentioned above include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, carbonyl, carbamido, carbamyl, carboxyl, thioureido, thiocyanato, sulfoamido, $C_1$~$C_6$ alkyl, $C_1$~$C_6$ alkenyl, $C_1$~$C_6$ alkoxy, aryl, heteroaryl, cyclyl, heterocyclyl, wherein alkyl, alkenyl, alkoxy, aryl, heteroaryl cyclyl, and heterocyclyl are optionally substituted with $C_1$~$C_6$ alkyl, aryl, heteroaryl, halogen, hydroxyl, amino, mercapto, cyano, or nitro.

As used herein, the term "alkyl" refers to a straight-chained or branched alkyl group containing 1 to 6 carbon atoms. Examples of alkyl groups include methyl (Me), ethyl (Et), n-propyl (Pr), isopropyl (i-Pr), tert-butyl, and n-pentyl.

The term "alkenyl" refers to a straight-chained or branched alkenyl group containing 2 to 6 carbon atoms. Examples of alkenyl groups include vinyl, allyl (2-propenyl), dimethylallyl, and butenyl.

The term "alkynyl" refers to a straight-chained or branched alkynyl group containing 2 to 6 carbon atoms. Examples of alkynyl groups include ethynyl and propargyl.

The term "aryl" refers to a hydrocarbon ring system (monocyclic or bicyclic) having at least one aromatic ring. Examples of aryl moieties include, but are not limited to, phenyl, naphthyl, and pyrenyl.

The term "heteroaryl" refers to a hydrocarbon ring system (monocyclic or bicyclic) having at least one aromatic ring which contains at least one heteroatom (e.g., O, N, or S) as part of the ring system. Examples of heteroaryl moieties include, but are not limited to, pyridinyl, triazolyl, tetrazolyl, pyrimidinyl, thiazolyl, indolyl, and indolizinyl.

The terms "cyclyl" and "heterocyclyl" refer to partially and fully saturated mono- or bi-cyclic rings having from 4 to 14 ring atoms. A heterocyclyl ring contains one or more heteroatoms (e.g., O, N, or S) as part of the ring. Exemplary cyclyl and heterocyclyl rings are cycylohexane, piperidine, piperazine, morpholine, thiomorpholine, and 1,4-oxazepane.

In another aspect, this invention features a pharmaceutical composition that contains a pharmaceutically acceptable carrier and an effective amount of at least one of the aforementioned compounds.

In further another aspect, the present invention features a method for treating an IL-12 overproduction-related disorder (e.g., rheumatoid arthritis, sepsis, Crohn's disease, multiple sclerosis, psoriasis, or insulin-dependent diabetes mellitus). The method includes administering to a subject in need thereof an effective amount of a compound of formula (I), wherein $R_1$ is aryl or heteroaryl; each of $R_2$ and $R_4$, independently, is H, halogen, CN, alkyl, $OR^a$, or $NR^aR^b$; $R_3$ is H, halogen, CN, alkyl, alkenyl, alkynyl, aryl, heteroaryl, cyclyl, heterocyclyl, $OR^a$, $OC(O)R^a$, $OC(O)NR^aR^b$, $NR^aR^b$, $NR^aC(O)R^b$, $NR^aS(O)R^b$, $NR^aS(O)_2R^b$, $NR^aC(O)NR^bR^c$, $NR^aC(S)NR^bR^c$, $NR^aC(NR^b)NR^cR^d$, $NR^aC(O)OR^b$, $S(O)NR^aR^b$, $S(O)_2NR^aR^b$, $S(O)R^a$, $S(O)_2R^a$, $C(O)R^a$, $C(O)OR^a$, $C(O)NR^aR^b$; $R_5$ is H or alkyl; n is 0, 1, 2, 3, 4, 5; or 6; A is O, S, S(O), $S(O)_2$, or $NR^e$; B is N or $CR^f$; X is O, S, S(O), $S(O)_2$, $NR^e$, or C(O); Y is a covalent bond, C(O), C=$NR^a$, O, S, S(O), $S(O)_2$, or $NR^e$; Z is N or CH; each of U and V, independently, is N or CR; and W is O, S, or $NR^e$; in which each of $R^a$, $R^b$, $R^c$, and $R^d$, independently, is H, alkyl, aryl, heteroaryl, cyclyl, or heterocyclyl; $R^e$ is H, alkyl, aryl, acyl, or sufonyl; and $R^f$ is H, alkyl, aryl, acyl, sulfonyl, alkoxyl, amino, ester, amide, CN, or halogen.

The structures of 55 above-described compounds are shown in Examples 1-55 below.

The compounds described above include the compounds themselves, as well as their salts and their prodrugs, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the compounds described above.

In addition, some of the compounds have one or more double bonds, or one or more asymmetric centers. Such compounds can occur as racemates, tautomers, racemic mixtures, single enantiomers, individual diastereomers, diastereomeric mixtures, and cis- or trans- or E- or Z-double isomeric forms.

Further, the aforementioned compounds also include their N-oxides. The term "N-okides" refers to one or more nitrogen atoms, when present in a compound, are in N-oxide form, i.e., N→O.

Also within the scope of this invention are a composition containing one or more of the compounds described above for use in treating an IL-12 overproduction-related disorder, and the use of such a composition for the manufacture of a medicament for the just-described use.

Other features, objects, and advantages of the invention will be apparent from the description and from the claims.

DETAILED DESCRIPTION

The compounds described above can be prepared by methods well known in the art, as well as by the synthetic routes disclosed herein. For example, a purine compound (i.e., each of U and V is N, A is $NR^e$, and B is N, U, V, A, B and $R^e$ are as defined in Summary) is prepared by using 2,4,8-trichloropurine as a starting material. The three chloro groups can be displaced by various substituents. More specifically, the most reactive chloro group (i.e., chloro at position 4) is substituted with a morpholino group to form morpholinopurine. Further reaction of morpholinopurine with a primary or secondary aromatic amine affords a desired compound. In another example, a purine compound is synthesized by reacting 4,8-dichloropuine subsequently with morpholine, a primary or secondary amine, halogen (e.g., bromine), and another primary or secondary amine, or an aryloxy agent (e.g., sodium phenoxide). In further another example, a compound described in Summary is prepared by reacting 3,4-diaminopyrimidine with an arylisocyanate (e.g., m-tolyl isocyanate) or aryldithioiminocarbonate (e.g., dimethyl N-(m-tolyl)-dithioiminocarbonate).

The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A compound thus obtained can be further purified by flash column chromatography, high performance liquid chromatography, or crystallization.

Also within the scope of this invention is a pharmaceutical composition that contains an effective amount of one or more of the compounds described in Summary and a pharmaceutically acceptable carrier. Further, the present invention covers a method of administering an effective amount of such a compound to a subject in need of treatment of IL-12 overproduction related diseases (e.g., rheumatoid arthritis, sepsis, Crohn's disease, multiple sclerosis, psoriasis, or insulin-dependent diabetes mellitus). The term "treating" is defined as the application or administration of a composition including the aforementioned compound to a subject, who has a IL-12 related disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Aidley, N.Y., 1970, 537. An effective amount of the compound described in Summary can range from about 0.001 mg/Kg to about 1000 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a compound described above, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile-injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A compound delineated herein can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds delineated herein, or one or more solubilizing agents, can be utilized as pharmaceutical excipients for delivery of the compounds. Examples of other carriers include colloidal silicon dioxide, magnesium stearate, cellulose, sodium lauryl sulfate, and D&C Yellow #10.

The biological activities of a compound delineated herein can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysacehardie or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A compound described above can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Preparation of {6-morpholin-4-yl-2-[2-(pyridin-2-yloxy)-ethoxy]-9H-purin-8-yl}-m-tolyl-amine

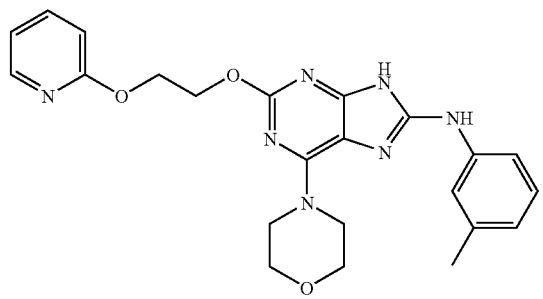

The title compound was synthesized by one of the following two methods:

Method A:

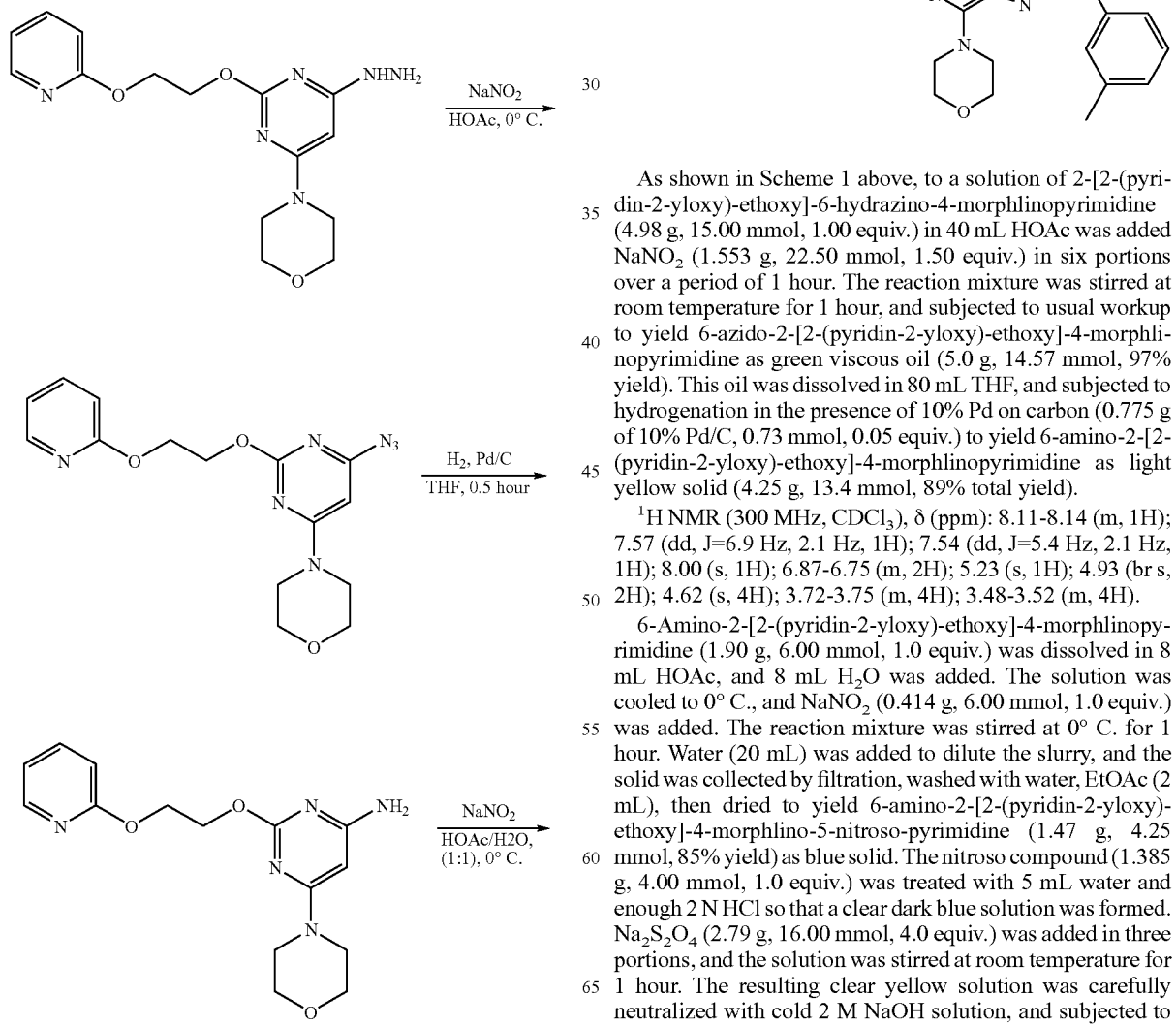

As shown in Scheme 1 above, to a solution of 2-[2-(pyridin-2-yloxy)-ethoxy]-6-hydrazino-4-morphlinopyrimidine (4.98 g, 15.00 mmol, 1.00 equiv.) in 40 mL HOAc was added NaNO$_2$ (1.553 g, 22.50 mmol, 1.50 equiv.) in six portions over a period of 1 hour. The reaction mixture was stirred at room temperature for 1 hour, and subjected to usual workup to yield 6-azido-2-[2-(pyridin-2-yloxy)-ethoxy]-4-morphlinopyrimidine as green viscous oil (5.0 g, 14.57 mmol, 97% yield). This oil was dissolved in 80 mL THF, and subjected to hydrogenation in the presence of 10% Pd on carbon (0.775 g of 10% Pd/C, 0.73 mmol, 0.05 equiv.) to yield 6-amino-2-[2-(pyridin-2-yloxy)-ethoxy]-4-morphlinopyrimidine as light yellow solid (4.25 g, 13.4 mmol, 89% total yield).

$^1$H NMR (300 MHz, CDCl$_3$), δ (ppm): 8.11-8.14 (m, 1H); 7.57 (dd, J=6.9 Hz, 2.1 Hz, 1H); 7.54 (dd, J=5.4 Hz, 2.1 Hz, 1H); 8.00 (s, 1H); 6.87-6.75 (m, 2H); 5.23 (s, 1H); 4.93 (br s, 2H); 4.62 (s, 4H); 3.72-3.75 (m, 4H); 3.48-3.52 (m, 4H).

6-Amino-2-[2-(pyridin-2-yloxy)-ethoxy]-4-morphlinopyrimidine (1.90 g, 6.00 mmol, 1.0 equiv.) was dissolved in 8 mL HOAc, and 8 mL H$_2$O was added. The solution was cooled to 0° C., and NaNO$_2$ (0.414 g, 6.00 mmol, 1.0 equiv.) was added. The reaction mixture was stirred at 0° C. for 1 hour. Water (20 mL) was added to dilute the slurry, and the solid was collected by filtration, washed with water, EtOAc (2 mL), then dried to yield 6-amino-2-[2-(pyridin-2-yloxy)-ethoxy]-4-morphlino-5-nitroso-pyrimidine (1.47 g, 4.25 mmol, 85% yield) as blue solid. The nitroso compound (1.385 g, 4.00 mmol, 1.0 equiv.) was treated with 5 mL water and enough 2 N HCl so that a clear dark blue solution was formed. Na$_2$S$_2$O$_4$ (2.79 g, 16.00 mmol, 4.0 equiv.) was added in three portions, and the solution was stirred at room temperature for 1 hour. The resulting clear yellow solution was carefully neutralized with cold 2 M NaOH solution, and subjected to EtOAc extraction. 5,6-Diamino-2-[2-(pyridin-2-yloxy)- ethoxy]-4-morphlinopyrimidine (0.80 g, 2.41 mmol, 60%) was obtained as light yellow solid after usual workup.

$^1$H NMR (300 MHz, CDCl$_3$), δ (ppm): 8.12-8.14 (m, 1H); 7.52-7.58 (m, 1H); 6.83-6.87 (m, 1H); 6.75-6.78 (m, 1H); 4.57-4.65 (m, 6H); 3.79-3.83 (m, 4H); 3.22-3.26 (m, 4H); 2.71 (br s, 2H).

ESMS calcd. for C$_{15}$H$_{21}$N$_6$O$_3$ 332.1; Found: 333.1 (M+H)$^+$.

5,6-Diamino-2-[2-(pyridin-2-yloxy)-ethoxy]4-morphlinopyrimidine (0.332 g, 1.00 mmol, 1.00 equiv.) and m-tolyl isocyanate (0.133 g, 1.00 mmol, 1.00 equiv.) were mixed in 10 mL THF and stirred at room temperature for 15 hours. THF was removed, and the residue was treated with POCl$_3$ in 2 mL CH$_3$NO$_2$ at 100° C. for 30 minutes. The reaction mixture was neutralized with 2N NaOH solution at 0° C., and subjected to EtOAc extraction. The organic solution was dried over MgSO4, filtered through a plug of silica gel, concentrated to around 2 mL, and cooled to 0° C., resulting in formation of the titled compound as off-white crystal which was collected by filtration, washed with EtOAc, and dried (0.095 g, 0.212 mmol, 21.2% yield).

$^1$H NMR (300 MHz, DMSO-d$_6$), δ (ppm): 11.70 (s, 1H); 9.10 (s, 1H); 8.16-8.18 (m, 1H); 7.69-7.75 (m, 1H); 7.43 (s, 1H); 7.35 (d, J=8.1 Hz, 1H); 7.14 (t, J=7.8 Hz, 1H); 6.97-7.01 (m, 1H); 6.85 (d, J=7.8 Hz, 1H); 6.71 (d, J=7.8 Hz, 1H); 4.52-4.57 (m, 4H); 4.09 (br s, 4H); 3.69-3.72 (m, 4H); 2.27 (s, 3H).

ESMS calcd. for C$_{23}$H$_{26}$N$_7$O$_3$: 447.2; Found: 448.2 (M+H)$^+$.

Method B:

Scheme 2

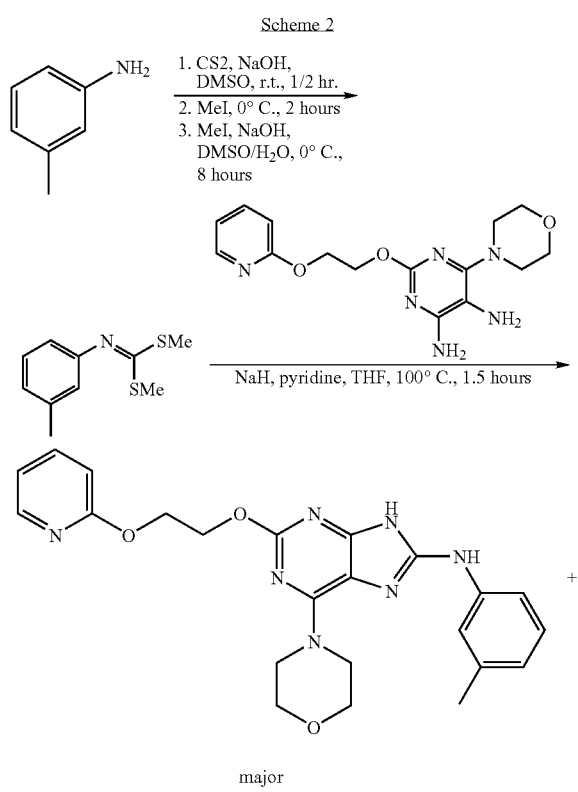

major

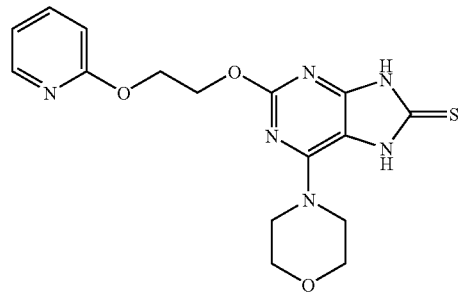

by-product, minor

As shown in Scheme 2 above, 5,6-diamino-2-[2-(pyridin-2-yloxy)-ethoxy]-4-morpholinopyrimidine (0.166 g, 0.5 mmol, 1.00 equiv.), dimethyl N-(m-tolyl)-dithioiminocarbonate (0.106 g, 0.5 mmol, 1.00 equiv., prepared from m-toluidine, CS$_2$, NaOH and MeI), pyridine (0.2 mL), and THF (5 mL) were mixed in a sealed tube. NaH (0.12 g 60% in oil, 3 mmol, 6.0 equiv) was added in the presence of nitrogen gas. The mixture was sealed in the tube, and heated at 100° C. for 1.5 hours. The titled compound was isolated as white solid (0.090 g, 0.20 mmol, 40% yield) after workup and purification. A side product, 6-morpholin-4-yl-2-[2-(pyridin-2-yloxy)-ethoxy]-7,9-dihydro-purine-8-thione, was also isolated as a white solid (0.018 g, 0.048 mmol, 10% yield).

EXAMPLE 2

Preparation of (3-methoxyphenyl)-{6-Morpholin-4-yl-2-[2-(pyridin-2-yloxy)-ethoxy]-9H-purin-8-yl}-amine

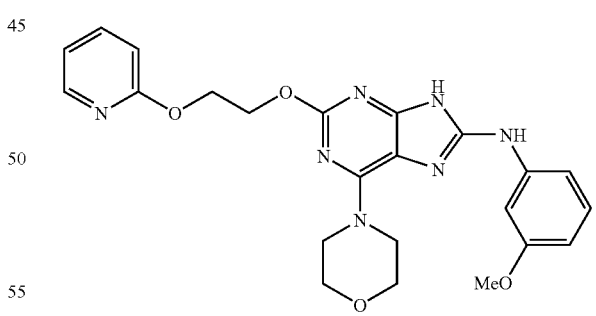

The title compound was synthesized as light brown solid in the same manner as described in Example 1, Method A.

$^1$H NMR (300 MHz, DMSO-d$_6$), δ (ppm): 11.73 (s, 1H), 9.28 (s, 1H), 8.16-8.18 (m, 1H), 7.69-7.75 (m, 1H), 7.58 (s, 1H), 7.15 (t, J=8.4 Hz, 1H), 6.97-7.01 (m, 2H), 6.85 (d, J=8.4 Hz, 1H), 6.44-6.47 (m, 1H), 4.50-4.60 (m, 4H), 4.10 (br s, 4H), 3.73 (s, 3H), 3.66-3.72 (m, 4H).

ESMS calcd for C$_{23}$H$_{24}$N$_7$O$_4$: 463.2; Found: 462.2(M−H)$^−$.

EXAMPLE 3

Preparation of {6-Morpholin-4-yl-2-[2-(pyridin-2-yloxy)-ethoxy]-9H-purin-8-yl}-p-tolyl-amine

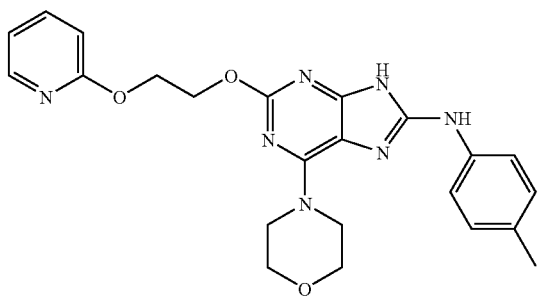

The title compound was synthesized as light brown solid in the same manner as described in Example 1, Method A.

$^1$H NMR (300 MHz, acetone-d$_6$), δ (ppm): 10.6 (s, 1H), 8.45 (br s, 1H), 8.11-8.20 (m, 1H), 7.58-7.70 (m, 3H), 7.05-7.15 (m, 2H), 6.92-6.97 (m, 1H), 6.75-6.80 (m, 1H), 4.57-4.67 (m, 4H), 4.18 (br s, 4H), 3.72-3.78 (m, 4H), 2.26 (s, 3H).

ESMS calcd for C$_{23}$H$_{26}$N$_7$O$_3$: 448.2; Found: 448.2 (M+H)$^+$.

EXAMPLE 4

Preparation of N$^2$-[2-(3,4-Dimethoxy-phenyl)-ethyl]-6-motpholin-4-yl-N$^8$-p-tolyl-9H-purine-2,8-diamine

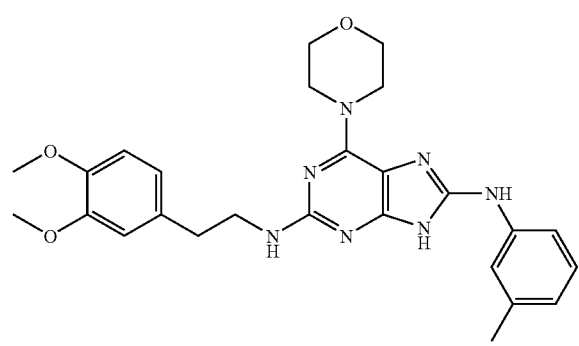

The title compound was synthesized by the method shown in Scheme 3

Scheme 3

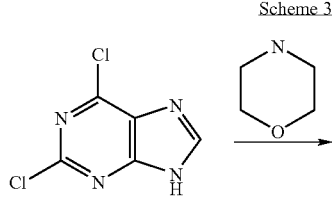

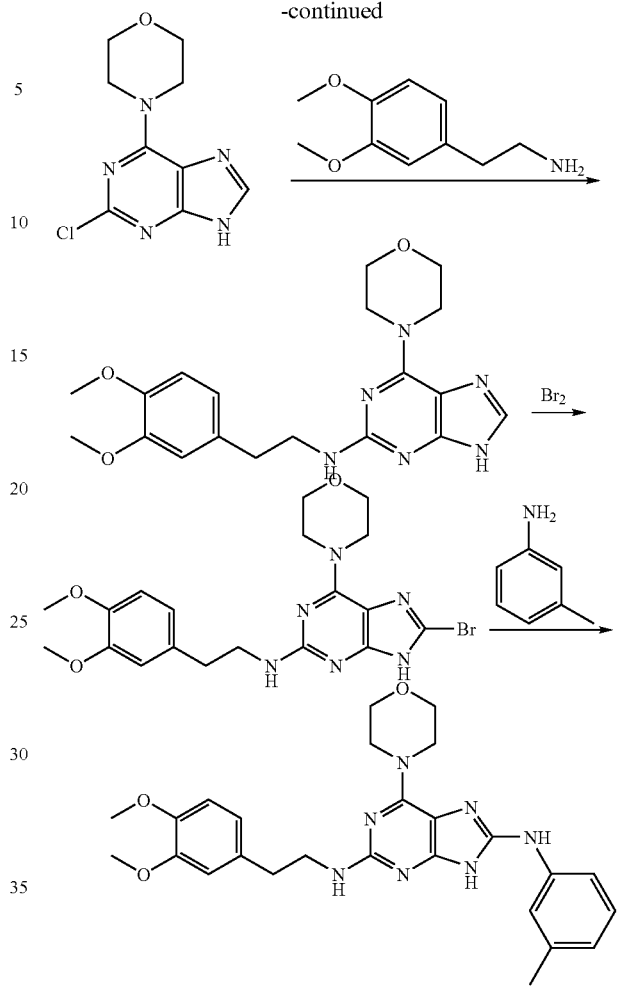

As shown in Scheme 3 above, a mixture of 2,6-dichloropurine (1.90 g, 10 mmol) and morpholine (2.34 g, 30 mmol) in water (25 mL) was heated under reflux for 15 min. Solidified reaction mixture was cooled to room temperature. Solid was filtered out and washed with water, methanol and ether. The 2-chloro-6-morpholin-4-yl-9H-purine was obtained in 96% yield (2.30 g). A mixture of 2-chloro-6-morpholin-4-yl-9H-purine (1.92 g, 8 mmol) and 2-(3,4-dimethoxyphenyl)ethylamine (4.35 g, 24 mmol) in sealed tube and under nitrogen was stirred at 190-195° C. for 1 hour. The reaction mixture turned to clear solution initially and then formed a slurry. The reaction mixture was cooled to room temperature diluted with methanol (8 mL) and the solid was collected by filtration, washed with methanol and Et$_2$O and dried to afford 2.30 g (74% yield) of [2-(3,4-dimethoxy-phenyl)-ethyl]-(6-morpholin-4-yl-9H-purin-2-yl)amine.

$^1$H NMR (DMSO-d$_6$) δ (ppm), 12.22 (bs, 1H), 7.69 (d, J=9.0 Hz, 1H), 6.86-6.73 (m, 3H), 6.30-6.22 (m, 1H), 4.12 (bs, 4H), 3.74-3.69 (m, 10H), 3.43 (t, J=6.0 Hz, 2H), 2.78-2.73 (m, 2H).

ESMS calcd for C$_{19}$H$_{24}$N$_6$O$_3$: 384.19; Found: 385.2 (M+H)$^+$.

To a solution of [2-(3,4-dimethoxy-phenyl)-ethyl]-(6-morpholin-4-yl-9H-purin-2-yl) amine (1.16 g, 3 mmol) in dioxane (75 mL) was added bromine (0.180 mL, 3.3 mmol) in dioxane (5 mL) dropwise over a period of 1 hour. The mixture was stirred at room temperature for additional 4 hours and diluted with water (25 mL) and extracted with EtOAc. The organic phase was washed with brine, water, dried over Na₂SO₄. The solvent was evaporated in vacuo and solid was washed with methanol to give (8-bromo-6-morpholin-4-yl-9H-purin-2-yl)-[2-(3,4-dimethoxy-phenyl)-ethyl]-amine as a white solid (1.05 g, 75% yield).

¹H NMR (DMSO-d₆) δ (ppm), 6.86-6.72 (m, 3H), 6.50-6.42 (m, 1H), 4.05 (bs, 4H), 3.75-3.69 (m, 10H), 3.44-3.38 (m, 2H), 2.78-2.74 (m, 2H).

ESMS calcd for C19H₂₃BrN₆O₃: 462.10; Found: 463.0 (M+H)⁺.

A mixture of (8-bromo-6-morpholin-4-yl-9H-purin-2-yl)-[2-(3,4-dimethoxy-phenyl)-ethyl]-amine (0.93 g, 2 mmol) and m-toluidine (0.86 mL, 8 mmol) in sealed tube and under nitrogen was stirred at 190-195° C. for 1 hour. The reaction mixture was cooled to room temperature diluted with methanol (5 mL) and the solid was collected by filtration, washed with small amount of methanol and Et₂O and dried to give 0.76 g of N²-[2-(3,4-Dimethoxy-phenyl)-ethyl]-6-morpholin-4-yl-N⁸-p-tolyl-9H-purine-2,8-diamine in 78% yield.

¹H NMR (DMSO-d₆) δ (ppm), 11.62 (bs, 1H), 9.46 (s, 1H), 7.38-7.18 (m, 4H), 6.86-6.70 (m, 4H), 3.82-3.34 (m, 16H), 2.77 (t, J=6.0 Hz, 2H), 2.27 (s, 3H).

ESMS calcd for C₂₆H₃₁N₇O₃: 489.25; Found: 490.2 (M+H)⁺.

EXAMPLE 5

Preparation of 6-morpholin-4-yl-N⁸-m-tolyl-9H-purine-2,8-diamine

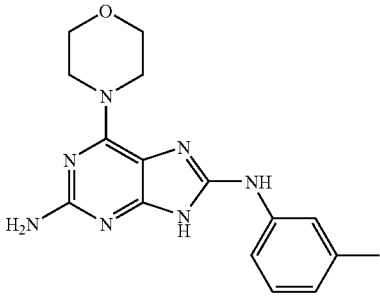

The title compound was prepared by a method as delineated herein.

¹H NMR (DMSO-d₆) δ (ppm), 9.15 (bs, 1H), 7.40-7.32 (m, 2H), 7.19-7.16 (m, 1H), 6.76-6.74 (m, 1H), 3.97 (bs, 4H), 3.74-3.72 (m, 4H), 2.27(s, 3H).

ESMS calcd for C₁₆H₁₉N₇O: 325.17; Found: 326.1 (M+H)⁺.

EXAMPLE 6

Preparation of 2-(6-morpholin-4-yl-8-m-tolylamino-9H-purin-2-ylamino)-ethanol

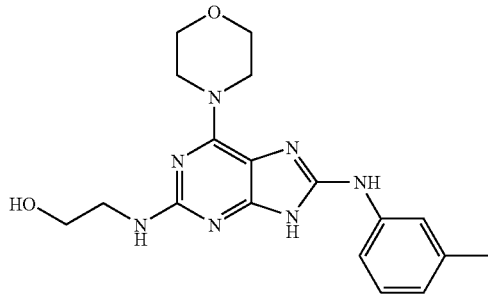

The title compound was prepared by a method as delineated herein.

¹H NMR (DMSO-d₆) δ (ppm), 11.64 (bs, 1H), 9.49 (s, 1H), 7.39-7.34 (m, 2H), 7.21 (t, J=7.2 Hz, 1H), 6.86-6.80 (m, 1H), 3.90-3.72 (m, 8H), 3.55 (t, J=6.0 Hz, 2H), 3.42-3.38 (m, 2H), 2.29 (s, 3H).

ESMS calcd for C₁₈H₂₃N₇O₂: 369.19; Found: 370.1 (M+H)⁺.

EXAMPLE 7

Preparation of N²-[2-(3,4-Dimethoxy-phenyl)-ethyl]-6-monpholin-4-yl-N⁸-m-tolyl-9H-purine-2,8-diamine

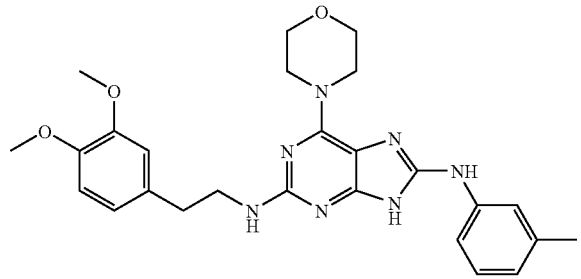

The title compound was prepared by a method as delineated herein.

¹H NMR (DMSO-d₆) δ (ppm), 11.65 (bs, 1H), 9.50 (s, 1H), 7.42-7.20 (m, 4H), 6.84-6.65 (m, 4H), 3.82-3.40 (m, 16H), 2.82-2.78 (m, 2H), 2.28(s, 3H).

ESMS calcd for C₂₆H₃₁N₇O₃: 489.25; Found: 490.2 (M+H)⁺.

EXAMPLE 8

Preparation of N²-[2-(3,4-dimethoxy-phenyl)-ethyl]-6-morpholin-4-yl-N⁸-p-tolyl-9H-purine-2,8-diamine

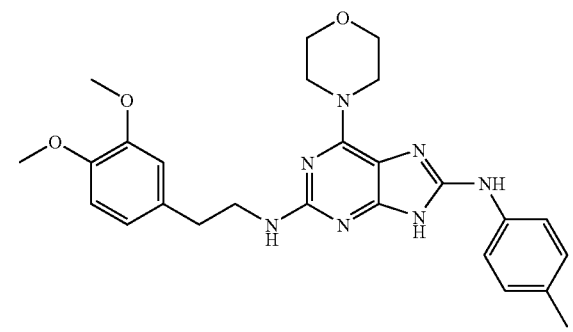

The title compound was prepared by a method as delineated herein.

¹H NMR (DMSO-d₆) δ (ppm), 11.62 (bs, 1H), 9.46 (s, 1H), 7.38-7.18 (m, 4H), 6.86-6.70 (m, 4H), 3.82-3.34 (m, 16H), 2.77 (t, J=6.0 Hz, 2H), 2.27(s, 3H).

ESMS calcd for C₂₆H₃₁N₇O₃: 489.25; Found: 490.2 (M+H)⁺.

EXAMPLE 9

Preparation of 9-methyl-6-morpholin-4-yl-N⁸-m-tolyl-9H-purine-2,8-diamine

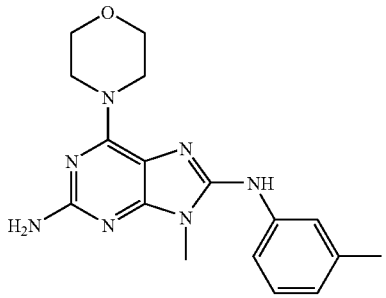

The title compound was prepared by a method as delineated herein.

¹H—NMR (DMSO-d$_6$) δ (ppm), 9.25 (bs, 1H), 7.40-7.32 (m, 2H), 7.22-7.16 (m, 2H), 6.76-6.72 (m, 1H), 3.97 (m, 7H), 3.74-3.72 (m, 4H), 2.27 (s, 3H).

ESMS calcd for $C_{17}H_{21}N_7O$: 339.18; Found: 340.2 (M+H)⁺.

EXAMPLE 10

Preparation of [2-(3,4-dimethoxy-benzyloxy)-6-morpholin-4-yl-9H-purin-8-yl]-p-tolyl-amine

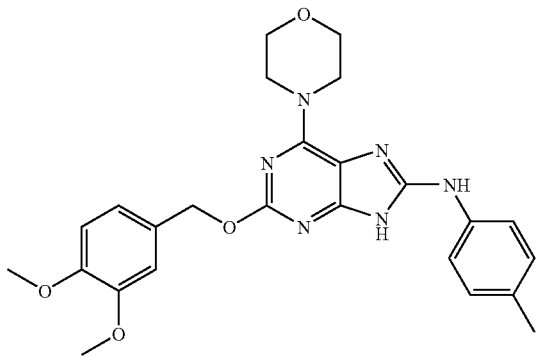

The title compound was prepared by a method as delineated herein.

¹H NM (DMSO-d$_6$) δ (ppm), 11.63 (s, 1H), 9.03 (s, 1H), 7.48-7.45 (m, 2H), 7.08-6.94 (m, 5H), 5.10 (s, 2H), 3.74-3.69 (m, 14H), 2.23 (s, 3H).

ESMS calcd for $C_{25}H_{28}N_6O_4$: 476.22; Found: 477.2 (M+H)⁺.

EXAMPLE 11

Preparation of N²-(4-methoxy-phenyl)-N²-methyl-6-morpholin-4-yl-N⁸-m-tolyl-9H-purine-2,8-diamine

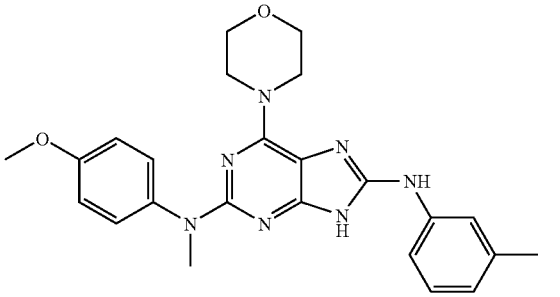

The title compound was prepared by a method as delineated herein.

¹H NMR (CDCl$_3$) δ (ppm), 9.37 (bs, 1H), 7.33-7.25 (m, 2H), 7.16-7.09 (m, 3H), 7.02-6.98 (m, 2H), 6.84-6.82 (m, 1H), 4.06-3.82 (m, 10H), 3.48-3.40 (m, 4H), 2.25 (s, 3H).

ESMS calcd for $C_{24}H_{27}N_7O_2$: 445.22; Found: 446.2 (M+H)⁺.

EXAMPLE 12

Preparation of N²-(4-methoxy-phenyl)-N²-methyl-9-methyl-6-morpholin-4-yl-N⁸-m-tolyl-9H-purine-2,8-diamine

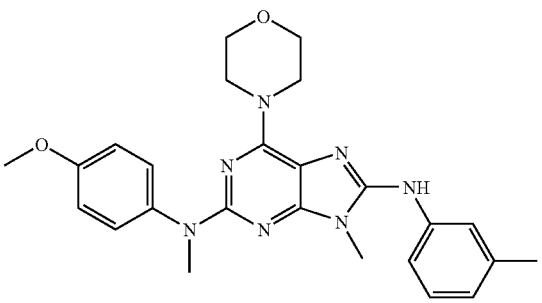

The title compound was prepared by a method as delineated herein.

¹H NMR (CDCl$_3$) δ (ppm), 7.38-7.07 (m, 5H), 6.95-6.8 (m, 3H), 5.94 (s, 1H), 4.20-4.05 (m, 4H), 3.81 (s, 3H), 3.78-3.75 (m, 4H), 3.51 (s, 3H), 3.44 (s, 3H), 2.30 (s, 3H).

ESMS calcd for $C_{25}H_{29}N_7O_2$: 459.24; Found: 460.2 (M+H)⁺.

EXAMPLE 13

Preparation of N²-[4-(2-Methoxy-ethoxy)-phenyl]-N²-methyl-6-morpholin-4-yl-N⁸-m-tolyl-9H-purine-2,8-diamine

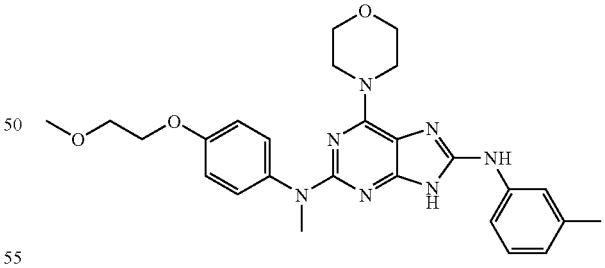

The title compound was prepared by a method as delineated herein.

¹H NMR (CDCl$_3$) δ (ppm), 9.20 (bs, 1H), 7.33-7.25 (m, 2H), 7.18-7.14 (m, 2H), 7.06-7.03 (m, 2H), 6.86-6.82 (m, 2H), 4.20-4.05 (m, 4H), 3.90-3.72 (m, 8H), 3.52 (s, 3H), 3.45 (s, 3H), 2.25 (s, 3H).

ESMS calcd for $C_{26}H_{31}N_7O_3$: 489.25; Found: 490.2 (M+H)⁺.

EXAMPLE 14

Preparation of 4-[2-(6-morpholin-4-yl-8-m-toly-lamino-9H-purin-2-ylamino)-ethyl]-benzenesulfonamide

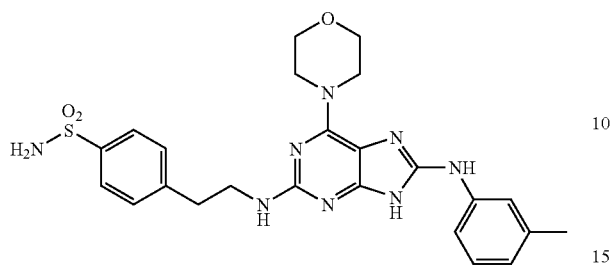

The title compound was prepared by a method as delineated herein.

$^1$H NMR (DMSO-$d_6$) δ (ppm), 11.64 (bs, 1H), 9.50(s, 1H), 7.73 (d, J=8.1 Hz, 2H), 7.42-7.17 (m, 8H), 6.82 (bs, 1H), 3.82-3.36 (m, 10H), 2.92 (t, J=7.2 Hz, 2H), 2.27 (s, 3H).

ESMS calcd for $C_{24}H_{28}N_8O_3S$: 508.20; Found: 509.2 (M+H)$^+$.

EXAMPLE 15

Preparation of 2-[methyl-(6-morpholin-4-yl-8-m-tolylamino-9H-purin-2-yl)-amino]-ethanol

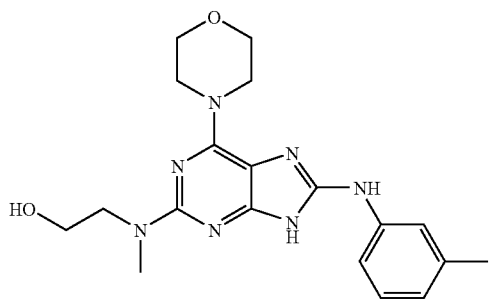

The title compound was prepared by a method as delineated herein.

$^1$H NMR (DMSO-$d_6$) δ (ppm), 9.60 (s, 1H), 7.43-7.22 (m, 3H), 6.86-6.82 (m, 1H), 6.60-6.50 (m, 1H), 4.33 (t, J=7.2 Hz, 2H), 3.94-3.72 (m, 10H), 2.99 (s, 3H), 2.29 (s, 3H).

ESMS calcd for $C_{19}H_{25}N_7O_2$: 383.21; Found: 384.2 (M+H)$^+$.

EXAMPLE 16

Preparation of 2-[(2-hydroxy-ethyl)-(6-morpholin-4-yl-8-m-tolylamino-9H-purin-2-yl)-amino]-ethanol

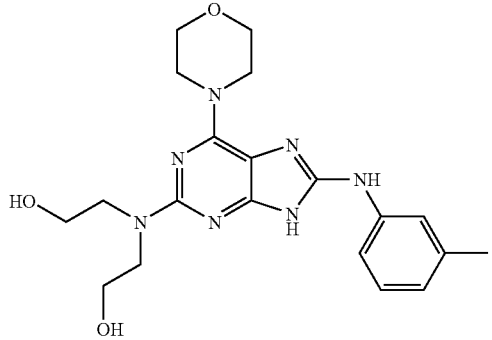

The title compound was prepared by a method as delineated herein.

$^1$H NMR (CDCl$_3$) δ (ppm), 10.62 (bs, 1H), 9.46(s, 1H), 7.38-7.07 (m, 4H), 4.24-4.15 (m, 4H), 3.94-3.90 (m, 4H), 3.82-3.77 (m, 8H), 2.27 (s, 3H).

ESMS calcd for $C_{20}H_{27}N_7O_3$: 413.22; Found: 414.4 (M+H)$^+$.

EXAMPLE 17

Preparation of 6-morpholin-4-yl-$N^2$,$N^8$-di-m-tolyl-9H-purine-2,8-diamine

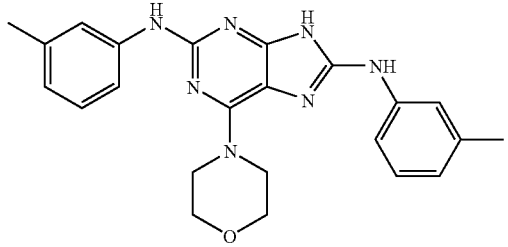

The title compound was prepared by the method shown in Scheme 4.

Scheme 4

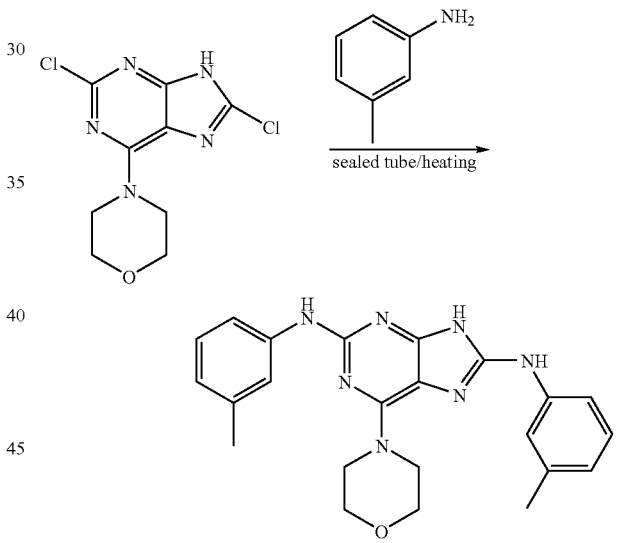

As shown in Scheme 4, a mixture of 2,8-dichloro-6-morpholin-4-yl-9H-purine (412 mg, 1.5 mmol) and m-tolylamine (0.97 mL, 9.0 mmol, 6 equiv.) was placed into a sealed tube filled with N$_2$. The sealed tube was submerged into an oil bath (180° C.). After 1.5 hours, the mixture in the sealed tube solidified. The sealed tube was cooled down to room temperature followed by adding ethyl acetate (10 mL) into the mixture. The resulting suspension was stirred for 1 hour at room temperature. The solid was collected by filtration and washed with cold methanol/water (5: 1) and ethyl acetate. A total of 480 mg pale yellow powder was obtained. Yield was 78%.

$^1$H NMR (CD$_3$OD) δ (ppm), 7.20-7.42 (m, 6H), 6.85-7.00 (m, 2H), 3.96-3.99 (m, 4H), 3.80-3.85 (m, 4H), 2.34-2.35 (m, 6H).

ESMS calcd for $C_{23}H_{25}N_7O$: 415.21; Found: 416.2 (M+H)$^+$.

EXAMPLE 18

Preparation of 6-morpholin-4-yl-$N^2,N^8$-di-o-tolyl-9H-purine-2,8-diamine

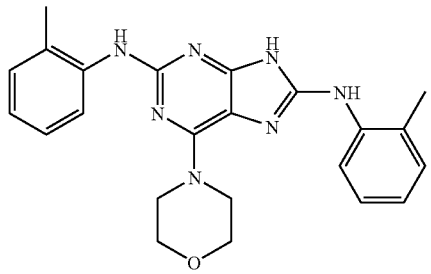

The title compound was prepared by a method as delineated herein.

$^1$H—NMR (CDCl$_3$) δ (ppm), 7.98 (br., 1H), 7.58 (br., 1H), 6.98-7.11 (m, 8H), 6.44 (br., 1H), 4.00-4.11 (m, 4H), 3.70-3.80 (m, 4H), 2.15-2.39 (m, 6H)/
ESMS calcd for C$_{23}$H$_{25}$N$_7$O: 415.21; Found: 416.2 (M+H)$^+$.

EXAMPLE 19

Preparation of 6-morpholin-4-yl-$N^2,N^8$-di-p-tolyl-9H-purine-2,8-diamine

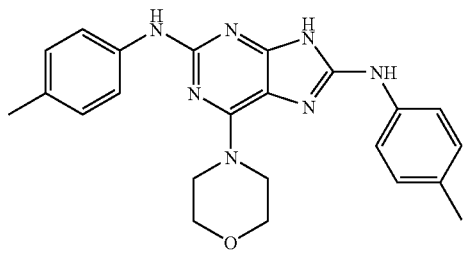

The title compound was prepared by a method as delineated herein.

$^1$H—NMR (CD$_3$OD) δ (ppm), 7.34-7.45 (dd, J=8.4, 25.8 Hz, 4H), 7.15-7.21 (dd, J=8.4, 9.0 Hz, 4H), 3.92 (m, 4H), 3.80-3.83 (m, 4H), 2.32-2.34 (m, 6H).
ESMS calcd for C$_{23}$H$_{25}$N$_7$O: 415.21; Found: 416.2 (M+H)$^+$.

EXAMPLE 20

Preparation of $N^2,N^8$-bis-(3,4-dimethoxy-phenyl)-6-morpholin-4-yl-9H-purine-2,8-diamine

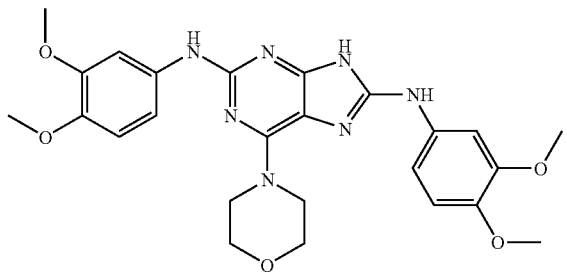

The title compound was prepared by a method as delineated herein.

$^1$H NMR (DMSO-d$_6$) δ (ppm), 7.43 (br., 1H), 7.27 (br., 1H), 6.34-7.09 (m, 7H), 3.75-4.00 (m, 20H).

ESMS calcd for C$_{25}$H$_{29}$N$_7$O$_5$: 507.22; Found: 508.2 (M+H)$^+$.

EXAMPLE 21

Preparation of $N^2,N^8$-bis-(3,4-dimethoxy-phenyl)-6-morpholin-4-yl-9H-purine-2,8-diamine

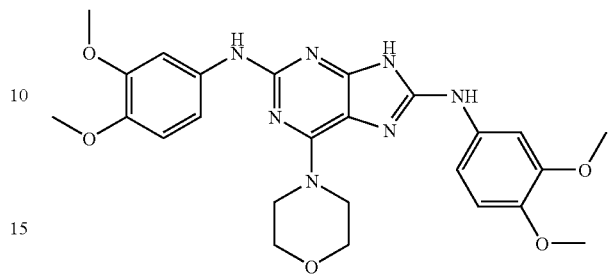

The title compound was prepared by a method as delineated herein.

$^1$H NMR (acetone-d$_6$) δ (ppm), 10.55 (br., 1H), 8.46 (d, J=8.1 Hz, 2H), 7.92 (br., 1H), 7.29 (br., 1H), 6.85 (m, 2H), 6.65 (m, 2H), 4.25 (m, 4H), 3.75-3.89 (m, 10H), 2.28 (m, 6H)/
ESMS calcd for C$_{25}$H$_{29}$N$_7$O$_3$: 475.23; Found: 476.2 (M+H)$^+$.

EXAMPLE 22

Preparation of $N^2,N^8$-bis-(3-methoxy-phenyl)-6-morpholin-4-yl-9H-purine-2,8-diamine

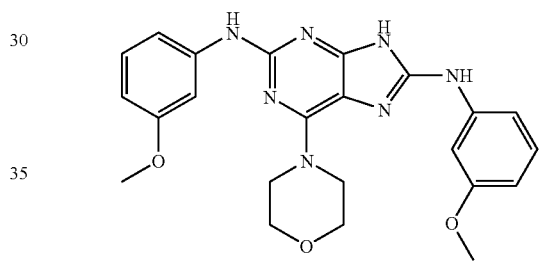

The title compound was prepared by a method as delineated herein.

$^1$H NMR (CD$_3$OD) δ (ppm), 7.19-7.35 (m, 4H), 7.02-7.05 (m, 2H), 6.64-6.74 (m, 2H), 4.00 (m, 4H), 3.80-3.85 (m, 10H).
ESMS calcd for C$_{23}$H$_{25}$N$_7$O$_3$: 447.20; Found: 448.2 (M+H)$^+$.

EXAMPLE 23

Preparation of 6-morpholin-4-yl-$N^2,N^8$-di-pyridin-3-yl-9H-purine-2,8-diamine

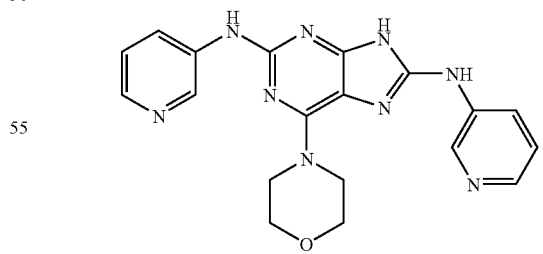

The title compound was prepared by a method as delineated herein.

$^1$H—NMR (CD$_3$OD) δ (ppm), 9.42 (s, 1H), 9.27 (d, J=5.4 Hz, 1H), 9.15 (s, 1H), 9.00 (d, J=5.4 Hz, 1H), 7.73-7.80 (m, 4H), 4.42 (m, 4H), 3.86-3.90 (m, 10H).
ESMS calcd for C$_{19}$H$_{19}$N$_9$O: 389.17; Found: 390.1 (M+H)$^+$.

EXAMPLE 24

Preparation of $N^2,N^8$-bis-(3-fluoro-phenyl)-6-morpholin-4-yl-9H-purine-2,8-diamine

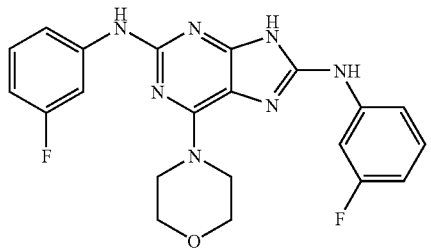

The title compound was prepared by a method as delineated herein.

$^1$H NMR (DMSO-d$_6$) δ (ppm), 9.58 (br., 1H), 9.28 (br., 1H), 7.78 (d, J=9.3 Hz, 1H), 7.59 (d, J=9.3 Hz, 1H), 7.25-7.42 (m, 4H), 6.68-6.71 (m, 2H), 4.09 (m, 4H), 3.75-3.77 (m, 4H)/

ESMS calcd for $C_{21}H_{19}F_2N_7O$: 423.16; Found: 424.1 (M+H)$^+$.

EXAMPLE 25

Preparation of $N^2,N^8$-bis-(4-methoxy-phenyl)-6-morpholin-4-yl-9H-purine-2,8-diamine

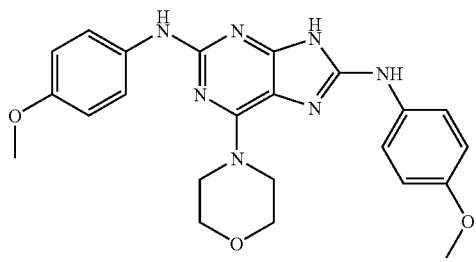

The title compound was prepared by a method as delineated herein.

$^1$H—NMR (MSO-d$_6$) δ (ppm), 9.40 (br., 2H), 7.52 (m, 4H), 6.90 (m, 4H), 3.60-3.90 (m, 14H).

ESMS calcd for $C_{23}H_{25}N_7O_3$: 447.20; Found: 448.2 (M+H)$^+$.

EXAMPLE 26

Preparation of $N^2,N^8$-bis-(3-ethoxy-phenyl)-6-morpholin-4-yl-9H-purine-2,8-diamine

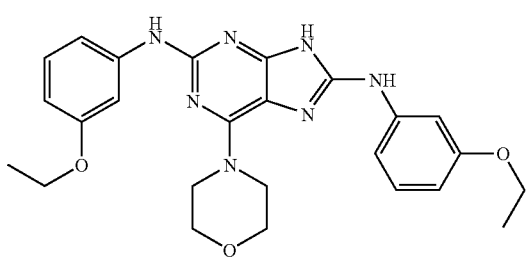

The title compound was prepared by a method as delineated herein.

$^1$H NMR (DMSO-d$_6$) δ (ppm), 9.40 (br., 2H), 7.48-7.54 (m, 2H), 6.90-7.20 (m, 4H), 6.55 (m, 2H), 3.75-4.10 (m, 12H), 1.33 (t, J=6.9 Hz, 6H).

ESMS calcd for $C_{25}H_{29}N_7O_3$: 475.23; Found: 476.2 (M+H)$^+$.

EXAMPLE 27

Preparation of $N^2,N^8$-bis-(3,5-dimethyl-phenyl)-6-morpholin-4-yl-9H-purine-2,8-diamine

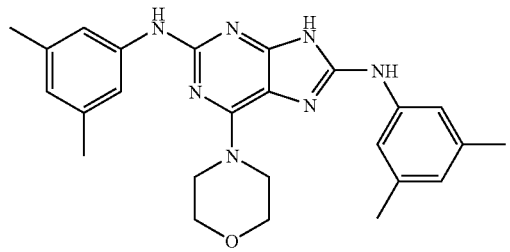

The title compound was prepared by a method as delineated herein.

$^1$H—NMR (CD$_3$OD/DMSO-d$_6$) δ (ppm), 7.37 (s, 4H), 7.22 (s, 4H), 6.55 (m, 2H), 6.49 (m, 2), 4.15 (m, 4H), 3.74-3.77 (m, 4H), 2.22 (m, 12H).

ESMS calcd for $C_{25}H_{29}N_7O$: 443.24; Found: 444.2 (M+H)$^+$.

EXAMPLE 28

Preparation of 9-methyl-6-morpholin-4-yl-$N^2,N^8$-di-m-tolyl-9H-purine-2,8-diamine

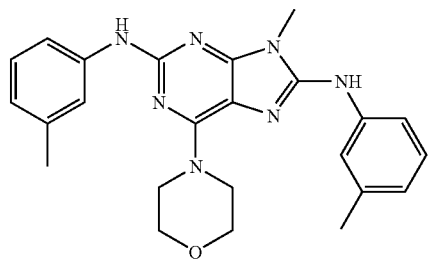

The title compound was prepared by a method as delineated herein.

$^1$H—NMR (CD$_3$OD) δ (ppm), 7.45 (m, 2H), 7.11-7.22 (m, 4H), 6.77-6.82 (m, 2H), 4.19 (m, 4H), 3.82 (m, 4H), 3.52 (s, 3H), 2.30 (m, 6H).

ESMS calcd for $C_{24}H_{27}N_7O$: 429.23; Found: 430.2 (M+H)$^+$.

EXAMPLE 29

Preparation of 6-Morpholin-4-yl-$N^2,N^8$-diphenyl-9H-purine-2,8-diamine

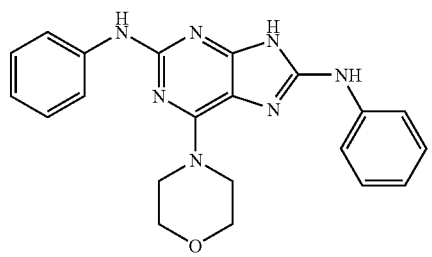

The title compound was prepared by a method as delineated herein.

$^1$H—NMR (DMSO-d$_6$) δ (ppm), 9.62 (br., 2H), 7.59 (m, 4H), 7.33 (m, 4H), 7.05 (m, 2H), 3.99 (m, 4H), 3.76 (m, 4H).

ESMS calcd for $C_{21}H_{21}N_7O$: 387.18; Found: 388.2 (M+H)$^+$.

EXAMPLE 30

Preparation of 6-morpholin-4-yl-N²,N⁸-bis-(3-trifluoromethyl-phenyl)-9H-purine-2,8-diamine

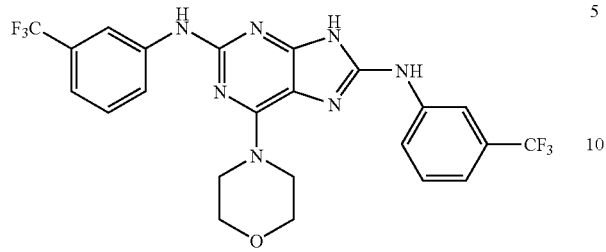

The title compound was prepared by a method as delineated herein.

¹H—NMR (DMSO-d$_6$) δ (ppm), 9.75 (br., 1H), 9.42 (br., 1H), 8.31 (m, 2H), 7.80 (m, 2H), 7.49 (m, 2H), 7.21 (m, 2H), 4.11 (m, 4H), 3.75 (m, 4H).

ESMS calcd for $C_{23}H_{19}F_6N_7O$: 523.16; Found: 524.2 (M+H)⁺.

EXAMPLE 31

Preparation of N²,N⁸-bis-(4-chloro-phenyl)-6-morpholin-4-yl-9H-purine-2,8-diamine

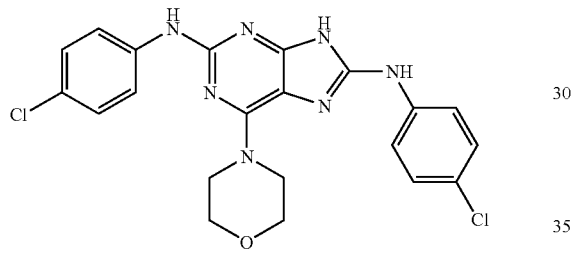

The title compound was prepared by a method as delineated herein.

¹H NMR (DMSO-d$_6$) δ (ppm), 9.75 (br., 2H), 7.64 (m, 4H), 7.36 (m, 4H), 4.02 (m, 4H), 3.75 (m, 4H).

ESMS calcd for $C_{21}H_{19}Cl_2N_7O$: 455.10; Found: 456.0 (M+H)⁺.

EXAMPLE 32

Preparation of N²,N⁸-bis-(4-methoxy-phenyl)-N², N⁸-dimethyl-6-morpholin-4-yl-9H-purine-2,8-diamine

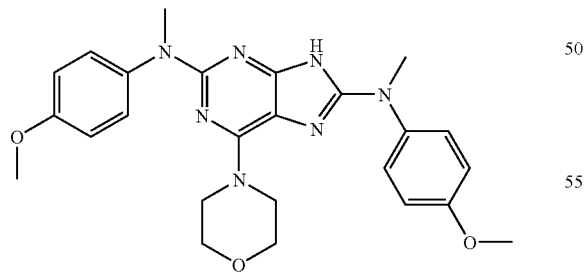

The title compound was prepared by a method as delineated herein.

¹H NMR (acetone-d$_6$) δ (ppm), 10.15 (br., 1H), 7.27 (AB, J=8.7 Hz, 2H) 7.21 (AB, J=8.7 Hz, 2H), 6.94 ((AB, J=8.7 Hz, 2H), 6.86 (AB, J=8.7 Hz, 2H), 4.04 (m, 4H), 3.79 (m, 6H), 3.68 (m, 4H), 3.38 (m, 6H).

ESMS clcd for $C_{25}H_{29}N_7O_3$: 475.23; Found: 476.5 (M+H)⁺.

EXAMPLE 33

Preparation of 3-bromo-4-(6-morpholin-4-yl-8-m-tolylamino-9H-purin-2-ylamino)-benzenesulfonamide

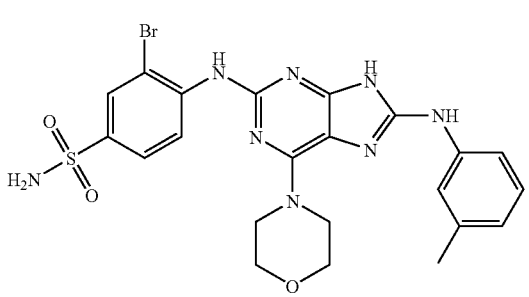

The title compound was prepared by a method as delineated herein.

¹H NMR (CD$_3$OD) δ (ppm), 8.68 (d, J=8.7 Hz, 1H), 8.04 (d, J=2.1 Hz, 1H), 7.76 (dd, J=2.1, 8.7 Hz, 1H), 7.49 (s, 1H), 7.34 (m, 1H), 7.16 (t, J=8.1 Hz, 1H), 6.77 (d, J=8.1 Hz, 1H), 4.18 (m, 4H), 3.83 (m, 4H), 2.30 (s, 3H).

ESMS calcd for $C_{22}H_{23}BrN_8O_3S$: 558.08; Found: 559.0 (M+H)⁺.

EXAMPLE 34

Preparation of N²-(4-methanesulfonyl-phenyl)-6-morpholin-4-yl-N⁸-m-tolyl-9H-purine-2,8-diamine

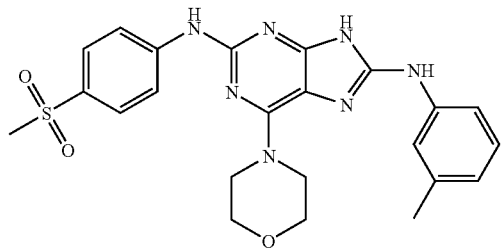

The title compound was prepared by a method as delineated herein.

¹H—NMR (DMSO-d$_6$) δ (ppm), 9.52 (br., 1H), 9.23 (br., 1H), 7.93 (m, 2H), 7.75 (m, 2H), 7.34-7.41 (m, 2H), 7.17 (m, 1H), 6.77 (m, 1H), 4.07 (m, 4H), 3.75 (m, 4H), 3.13 (s, 3H), 2.28 (s, 3H).

ESMS calcd for $C_{23}H_{25}N_7O_3S$: 479.17; Found: 480.2 (M+H)⁺.

EXAMPLE 35

Preparation of 4[-methyl-(6-morpholin-4-yl-8-m-tolylamino-9H-purin-2-yl)-amino]-benzonitrile

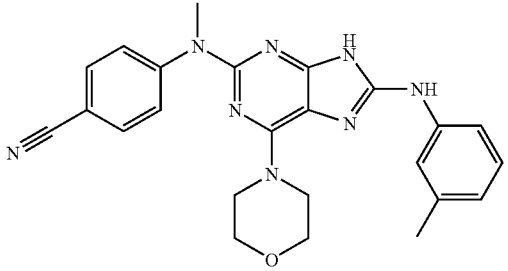

The title compound was prepared by a method as delineated herein.

¹H NMR (CD$_3$OD) δ (ppm), 7.37-7.59 (m, 6H), 7.21 (m, 1H), 6.81 (m, 1H), 4.15 (m, 4H), 3.83 (m, 4H), 3.59 (s, 3H), 2.35 (s, 3H).

ESMS calcd for $C_{24}H_{24}N_8O$: 440.21; Found: 441.2 (M+H)⁺.

EXAMPLE 36

Preparation of N²-dimethyl-6-morpholin-4-yl-N², N⁸-di-m-tolyl-9H-purine-2,8-diamine

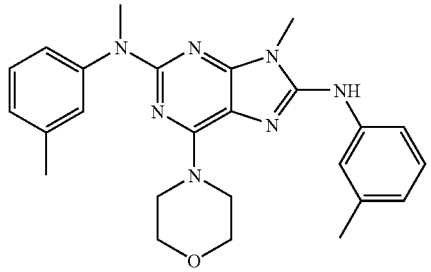

The title compound was prepared by a method as delineated herein.

¹H NMR (DMSO-d$_6$) δ (ppm), 9.58 (br., 2H), 7.58 (m, 1H), 7.52 (s, 1H), 7.38 (s, 1H), 7.24-7.28 (m, 3H), 6.91-6.99 (m, 2H), 3.84 (s, 3H), 3.69 (m, 4H), 3.65 (s, 3H), 3.58 (m, 4H), 2.34 (s, 3H), 2.32 (s, 3H).

ESMS calcd for $C_{25}H_{29}N_7O$: 443.24; Found: 444.2 (M+H)⁺.

EXAMPLE 37

Preparation of [2-(4-Fluoro-phenoxy)-6-morpholin-4-yl-9H-purin-8-yl]-m-tolyl-amine

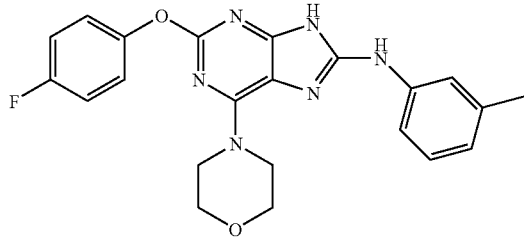

The title compound was prepared by a method as delineated herein.

¹H NMR (acetone-d$_6$) δ (ppm), 10.68 (s, 1H), 8.55 (s, 1H), 7.56 (s, 1H), 7.48 (d, J=8.4 Hz, 1H), 7.19-7.14 (m, 5H), 6.78 (d, J=7.2 Hz, 1H), 4.12 (m, 4H), 3.75 (m, 4H), 2.30 (s, 3H).

ESMS calcd for $C_{22}H_{21}FN_6O_2$: 420.17; Found: 421.1 (M+H)⁺.

EXAMPLE 38

Preparation of (6-morpholin-4-yl-2-p-tolyloxy-9H-purin-8-yl)-m-tolyl-amine

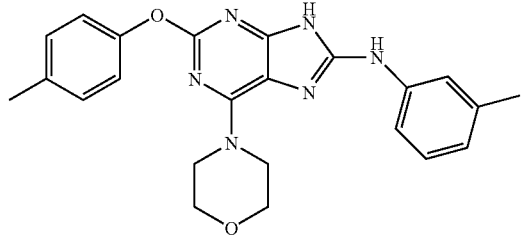

The title compound was prepared by a method as delineated herein.

¹H NMR (acetone-d$_6$) δ (ppm), 10.60 (s, 1H), 8.59 (s, 1H), 7.56 (s, 1H), 7.48 (d, J=9.0 Hz, 1H), 7.27-7.13 (m, 4H), 7.02 (d, J=8.4 Hz, 1H), 6.77 (d, J=8.4 Hz, 1H), 4.14 (m, 4H), 3.75 (m, 4H), 2.33 (s, 3H), 2.30 (s, 3H).

ESMS calcd for $C_{23}H_{24}N_6O_2$: 416.20; Found: 417.2 (M+H)⁺.

EXAMPLE 39

Preparation of (2-chloro-6-morpholin-4-yl-9H-purin-8-yl)-m-tolyl-amine

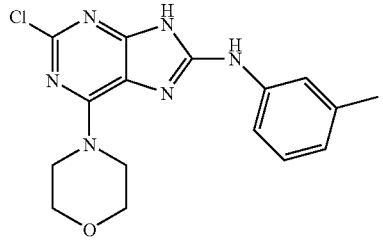

The title compound was prepared by a method as delineated herein.

¹H NMR (DMSO-d$_6$) δ (ppm), 12.00 (brs, 1H), 9.39 (s, 1H), 7.45 (s, 1H), 7.37 (d, J=8.1 Hz, 1H), 7.16 (t, J=7.6 Hz, 1H), 6.75 (d, J=7.2 Hz, 1H), 4.09 (m, 4H), 3.72 (m, 4H), 2.27 (s, 3H).

ESMS calcd for $C_{16}H_{17}ClN_6O$: 344.12; Found: 345.2 (M+H)⁺.

EXAMPLE 40

Preparation of 3-(6-morpholin-4-yl-8-m-tolylamino-9H-purin-2-ylamino)-phenol

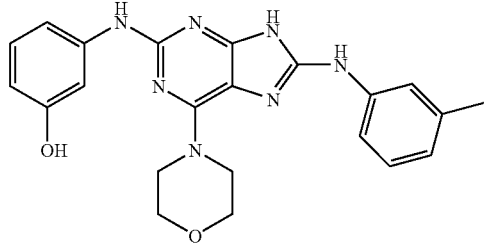

The title compound was prepared by a method as delineated herein.

¹H NMR (acetone-d$_6$) δ (ppm), 10.46 (brs, 1H), 8.39 (s, 1H), 8.09 (s, 1H), 7.84 (s, 1H), 7.56 (s, 1H), 7.49-7.45 (m, 2H), 7.18 (brd, J=8.7 Hz, 1H), 7.15 (t, J=7.8 Hz, 1H), 7.02 (t, J=8.0 Hz, 1H), 6.75 (brd, J=6.9 Hz, 1H), 6.37 (ddd, J=7.4, 2.1 and 0.8 Hz, 1H), 4.19 (m, 4H), 3.77 (m, 4H), 2.30 (s, 3H).

ESMS calcd for $C_{22}H_{23}N_7O_2$: 417.19; Found: 418.2 (M+H)⁺.

EXAMPLE 41

Preparation of 4-(6-morpholin-4-yl-8-m-tolylamino-9H-purin-2-yloxy)-benzonitrile

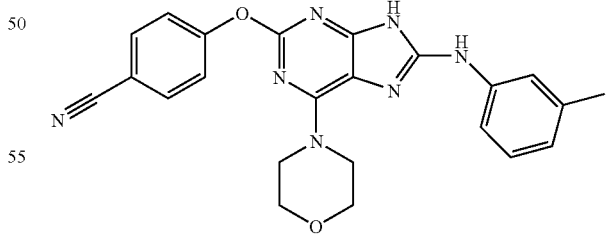

The title compound was prepared by a method as delineated herein.

¹H NMR (acetone-d$_6$) δ (ppm), 10.71 (brs, 1H), 8.61 (s, 1H), 7.81 (m, J$_{AA'}$=8.7 Hz, 2H), 7.56 (s, 1H), 7.49 (brd, J=7.5 Hz, 1H), 7.36 (m, J$_{AA'}$=8.7 Hz, 2H), 7.17 (t, J=8.0 Hz, 1H), 6.79 (d, J=7.5 Hz, 1H), 4.14 (m, 4H), 3.74 (m, 4H), 2.30 (s, 3H).

ESMS calcd for $C_{23}H_{21}N_7O_2$: 427.18; Found: 428.2 (M+H)⁺.

EXAMPLE 42

Preparation of [2-(4-Methoxy-phenoxy)-6-morpholin-4-yl-9H-purin-8-yl]-m-tolyl-amine

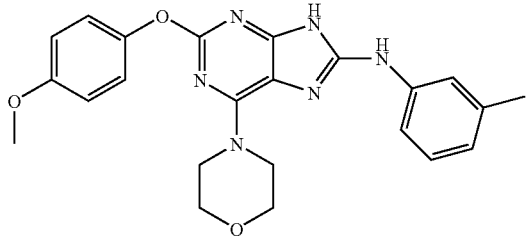

The title compound was prepared by a method as delineated herein.

$^1$H NMR (acetone-d$_6$) δ (ppm), 10.63 (brs, 1H), 8.54 (s, 1H), 7.55 (s, 1H), 7.48 (brd, J=9.0 Hz, 1H), 7.16 (t, J=7.6 Hz, 1H), 7.07 (m, J$_{AA'}$=9 Hz, 2H), 6.93 (m, J$_{BB'}$=9.3 Hz, 2H), 6.76 (d, J=7.2 Hz, 1H), 4.12 (m, 4H), 3.80 (s, 3H), 3.75 (m, 4H), 2.29 (s, 3H).

ESMS calcd for C$_{23}$H$_{24}$N$_6$O$_3$: 432.19; Found: 433.2 (M+H)$^+$.

EXAMPLE 43

Preparation of N-(6-morpholin-4-yl-8-m-tolylamino-9H-purin-2-yl)-2-(pyridin-3-yloxy)-acetamide

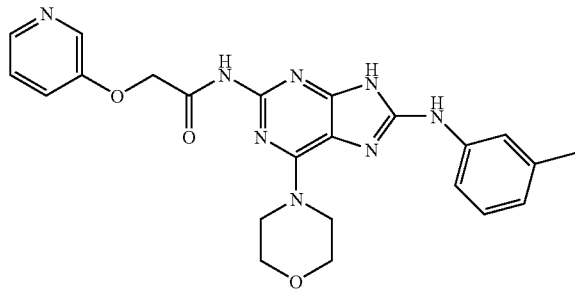

The title compound was prepared by a method as delineated herein.

$^1$H NMR (DMSO-d$_6$) δ (ppm), 10.08 (s, 1H), 9.2 (s, 1H), 8.31 (s, 1H), 8.18 (m, 1H), 7.46-7.35 (m, 4H), 7.15 (t, J=7.6 Hz, 1H), 6.73 (d, J=8.1 Hz, 1H), 5.10 (s, 2H), 4.11 (m, 4H), 3.73 (m, 4H), 2.27 (s, 3H).

ESMS calcd for C$_{23}$H$_{24}$N$_8$O$_3$: 460.20; Found: 461.2 (M+H)$^+$.

EXAMPLE 44

Preparation of {6-morpholin-4-yl-2-[2-(pyridin-3-yloxy)-ethoxy]-9H-purin-8-yl]-m-tolyl-amine

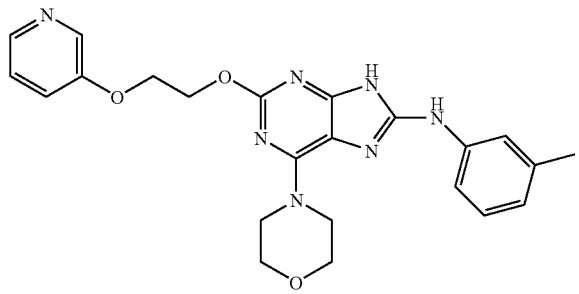

The title compound was prepared by a method as delineated herein.

$^1$H NMR (DMSO-d$_6$) δ (ppm), 11.75 (s, 1H), 9.12 (s, 1H), 8.34 (s, 1H), 8.19 (d, J=4.3 Hz, 1H), 7.46-7.35 (m, 4H), 7.17 (t, J=7.6 Hz, 1H), 6.71 (d, J=8.1 Hz, 1H), 4.54 (m, 2H), 4.38 (m, 2H), 4.08 (m, 4H), 3.71 (m, 4H), 2.27 (s, 3H).

ESMS calcd for C$_{23}$H$_{25}$N$_7$O$_3$: 447.20; Found: 448.5 (M+H)$^+$.

EXAMPLE 45

Preparation of 6-morpholin-4-yl-N$^2$-(3-phenyl-propyl)-N$^8$-m-tolyl-9H-purine-2,8-diamine

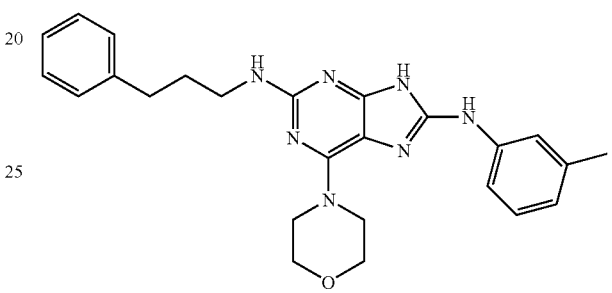

The title compound was prepared by a method as delineated herein.

$^1$H NMR (acetone-d$_6$) δ (ppm), 8.34 (brs, 1H), 7.52-7.14 (m, 9H), 6.71 (s, 1H), 5.63 (brs, 1H), 4.11 (m, 4H), 3.73 (m, 4H), 3.38 (m, 2H), 2.67 (t, J=7.8 Hz, 2H), 2.25 (s, 3H), 1.90 (qv, J=7.5 Hz, 2H).

ESMS calcd for C$_{25}$H$_{29}$N$_7$O: 443.24; Found: 444.2 (M+H)$^+$.

EXAMPLE 46

Preparation of N-(6-morpholin-4-yl-8-p-tolylamino-7H-purin-2-yl)-acetamide

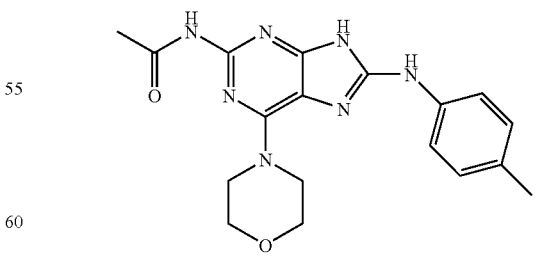

The title compound was prepared by a method as delineated herein.

$^1$H NMR (DMSO-d$_6$) δ (ppm), 11.79 (brs, 1H), 9.77 (s, 1H), 9.14 (s, 1H), 7.49 (d, J=7.8 Hz, 2H), 7.08 (d, J=7.8 Hz, 2H), 4.09 (m, 4H), 3.71 (m, 4H), 2.24 (s, 3H), 2.16 (s, 3H).

ESMS calcd for C$_{18}$H$_{21}$N$_7$O$_2$: 367.18; Found: 368.2 (M+H)$^+$.

EXAMPLE 47

Preparation of N-2',N-8'-Bis-(3-ethyl-phenyl)-6-morpholin-4-yl-7H-purine-2,8-diamine

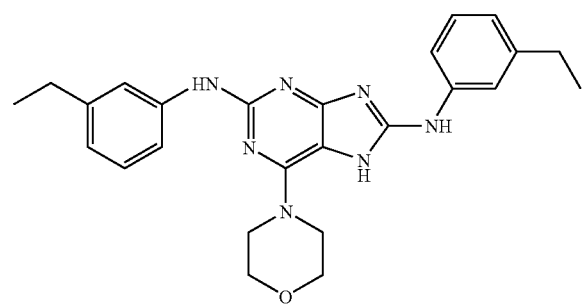

The title compound was prepared by a method as delineated herein.

$^1$H NM (DMSO-d$_6$) δ (ppm), 9.43 (s, 1H), 7.63 (s, 1H), 7.31 (d, J=8.7 Hz, 1H), 7.18 (dd, J$_1$=8.7 Hz, J$_2$=6.9 Hz, 1H), 6.78 (d, J=6.9 Hz), 4.11 (bs, 4H), 3.72 (bs 4H), 2.58 (q, J=7.5 Hz, 2H), 1.18 (t, J=7.5 Hz, 3H).

ESMS calcd for C$_{25}$H$_{29}$N$_7$O: 443.24; Found: 444.1 (M+H)$^+$.

EXAMPLE 48

Preparation of (4-methoxy-phenyl)-methyl-(6-morpholin-4-yl-8-m-tolyloxy-7H-purin-2-yl)-amine

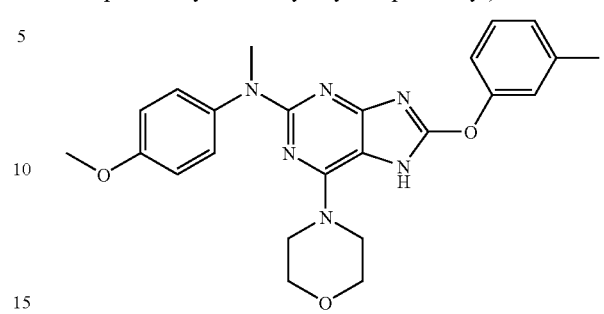

The title compound was prepared by a method as delineated herein.

$^1$H NMR (CDCl$_3$) δ (ppm), 7.26-7.21 (m, 3H), 7.07-7.04 (m, 2H), 6.97 (d, J=7.2 Hz, 1H), 4.02 (bs, 4H), 3.78 (s, 3H), 3.73 (m, 4H), 3.49 (s, 3H), 3.32 (s, 3H).

ESMS calcd for C$_{24}$H$_{26}$N$_6$O$_3$: 446.21; Found: 447.1 (M+H)$^+$.

EXAMPLE 49

Preparation of (2,6-di-morpholin-4-yl-7H-purin-8-yl)-m-tolyl-methanone

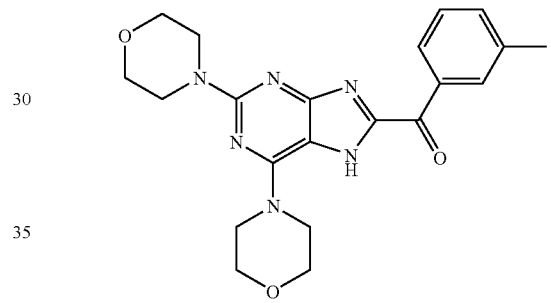

The title compound was synthesized by the method shown in Scheme 5.

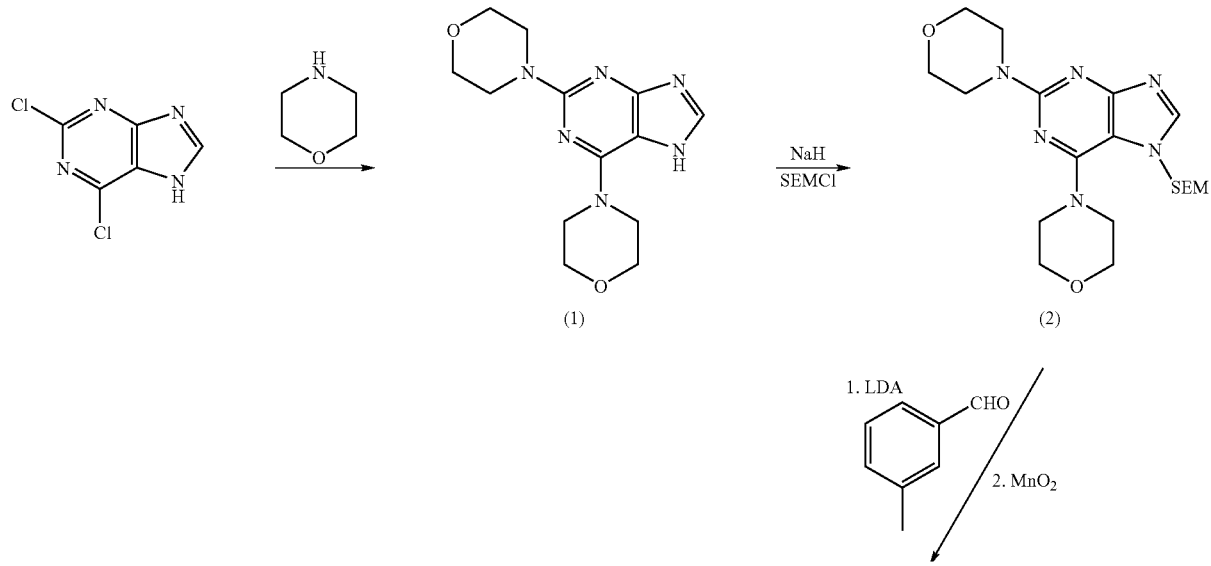

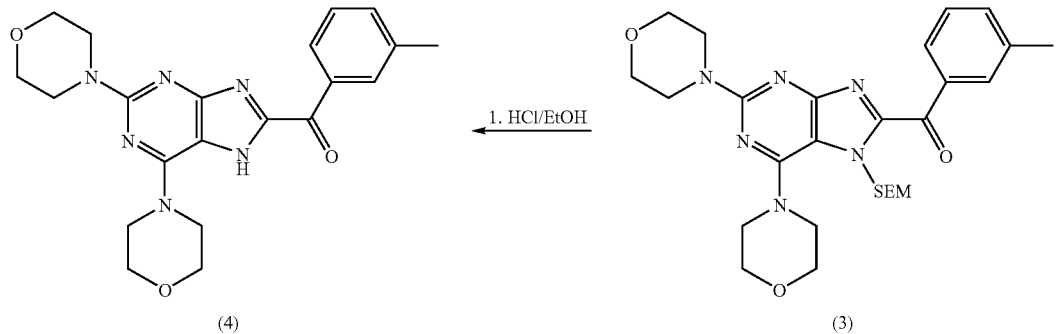

As shown in Scheme 5 above, 2,6-dicloropyrimidine (1 g, 5.29 mmol) was dissolved in morpholine (5 mL) in a sealed tube. The tube was heated to 120° C. for 5 hours then cooled to room temperature. Water (100 mL) was added and the resulting precipitate was filtered and washed with water to give 2,6-di-morpholin-4-yl-7H-purine (1.33 g, 87%). 2,6-Di-morpholin-4-yl-7H-purine (1.33 g, 4.58 mmol) was dissolved in DMF (50 mL). NaH (0.22 g, 5.50 mmol, 60% dispersion in oil) was added and the reaction was stirred at room temperature for 30 min. 2-(Trimethylsilyl)ethoxymethyl chloride (0.92 g, 5.50 mmol) was added dropwisely and the reaction was stirred for 18 h at room temperature. Water (200 mL) then ethyl aceate (200 mL) were added. The ethyl acetate extracts were washed with water (3×100 mL), dried over MgSO$_4$, filtered and evaporated to dryness. The resulting residue was purified by silicagel column chromatography eluting with a gradient of 1:1 ethyl aceate to ethyl acetate to produce 2,6-Di-morpholin-4-yl-7-(2-trimethylsilanylethoxymethyl)-7H-purine (1.51 g, 78% yield).

$^1$H NMR (DMSO-d$_6$) δ (ppm), 8.23 (s, 1H), 8.18 (d, J=7.1 Hz, 1H), 7.22-7.18 (m, 4H), 6.97 (d, J=9.3 Hz, 2H), 5.78 (s, 1H), 4.15 (bs, 4H), 3.80-3.78 (m, 7H), 3.43 (s, 3H), 2.33 (s, 3H).

ESMS calcd for C$_{19}$H$_{32}$N$_6$O$_3$Si: 420.23; Found: 421.2 (M+H)$^+$.

2,6-Di-morpholin-4-yl-7-(2-trimethylsilanylethoxymethyl)-7H-purine (266 mg, 0.63 mmol) was dissolved in dry TBF (10 mL) and cooled to –78 C. A solution of LDA (0.38 mL, 0.76 mmol, 2 M solution in heptane) was added dropwisely then the reaction was stirred at –78 C for 30 min. To the resulting suspension was added a solution of m-tolylaldehyde (114 mg, 0.95 mmol) in THF (5 mL) then the reaction was stirred for 1 hour. Saturated NH$_4$Cl (50 mL) was added then the reaction was allowed to warm to room temperature. THF was removed under reduced pressure then ethyl acetate (50 mL) was added. The ethyl acetate layer was washed with water (3×50 mL), dried over MgSO$_4$ then evaporated to dryness.

The crude product was purified by silcagel column chromatography. Elution with 25% ethyl aceate/hexane produced [2,6-di-morpholin-4-yl-7-(2-trimethylsilanyl-ethoxymethyl)-7H-purin-8-yl]-m-tolyl-methanone (198 mg, 56% yield).

$^1$H NMR (CDCl$_3$) δ (ppm), 8.11 (s, 1H), 8.07 (d, J=7.2 Hz, 1H), 7.40-7.39 (m, 2H), 5.95 (s, 2H), 3.84-3.78 (m, 16H), 3.68-3.63 (m, 2H), 2.43 (s, 3H), 0.97-0.91 (m, 2H), -0.08 (s, 9H).

ESMS calcd for C$_{27}$H$_{38}$N$_6$O$_4$Si: 538.27; Found: 539.2 (M+H)$^+$.

[2,6-Di-morpholin-4-yl-7-(2-trimethylsilanyl-ethoxymethyl)-7H-purin-8-yl]-m-tolyl-methanone (185 mg, 0.34 mmol) was dissolved in ethanol (10 ml) and 2N HCl (4 mL). The resulting suspension was heated to reflux for 4 hrs then cooled to room temperature. After neutralization with 2N NaOH, ethanol was removed under reduced pressure and ethyl acetate (100 mL) was added. The ethyl acetate layer was washed with water (3×50 mL), dried over MgSO$_4$ then evaporated to dryness. The crude product was purified by silcagel column chromatography. Elution with a gradient of 25% ethyl aceate/hexane to ethyl acetate to 10% methanol/ethyl aceate produced (2,6-di-morpholin-4-yl-7H-purin-8-yl)-m-tolyl-methanone (80 mg, 57% yield).

$^1$H NMR (DMSO-d$_6$) δ (ppm), 8.34 (s, 1H), 8.28 (d, J=7.5 Hz, 1H), 7.62-7.58 (m, 2H), 3.89-3.80 (m, 16H), 2.54 (s, 3H).

ESMS calcd for C$_{21}$H$_{24}$N$_6$O$_3$: 408.19; Found: 409.1 (M+H)$^+$.

EXAMPLE 50

Preparation of {2-[(4-Methoxy-phenyl)-methylamino]-6-morpholin-4-yl-7H-purin-8-yl}-m-tolyl-methanone

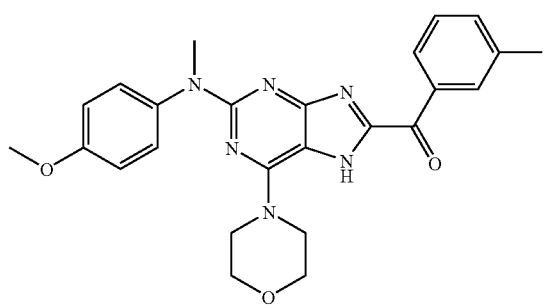

The title compound was prepared by a method as delineated herein.

$^1$H NMR (DMSO-d$_6$) δ (ppm), 8.19 (s, 1H), 8.12 (d, J=7.5 Hz, 1H), 7.46-7.43 (m, 2H), 7.25 (d, J=9.3 Hz, 2H), 6.93 (d, J=9.3 Hz, 2H), 4.04 (bs, 4H), 3.77 (s, 3H), 3.70 (bs, 4H), 3.43 (s, 3H), 2.39 (s, 3H).

ESMS calcd for C$_{25}$H$_{26}$N$_6$O$_3$: 458.21; Found: 459.1 (M+H)$^+$.

EXAMPLE 51

Preparation of (4-fluoro-5,7-di-morpholin-4-yl-1H-s-yl)-m-tolyl-amine

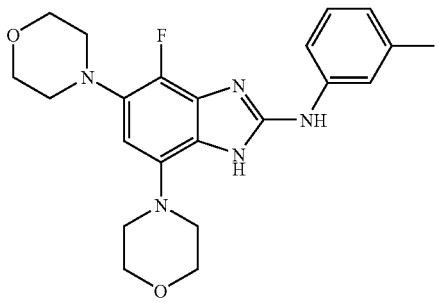

The title compound was prepared by a method as delineated herein.

$^1$H NMR (DMSO-d$_6$) δ (ppm), 7.5-7.1 (m, 5H), 3.89-3.80 (m, 16H), 2.54 (s, 3H), ESMS calcd for C$_{22}$H$_{26}$FN$_5$O$_2$: 411.2; Found: 412.1 (M+H)$^+$.

EXAMPLE 52

Preparation of [2-(2-methoxy-ethyl)-6-morpholin-4-yl-9H-purin-8-yl]-m-tolyl-amine

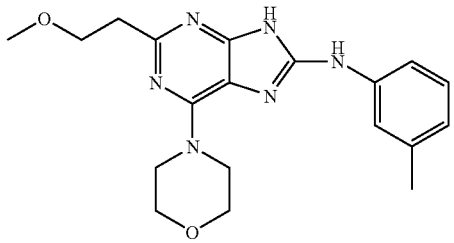

The title compound was prepared by the method shown in Scheme 6.

Scheme 6

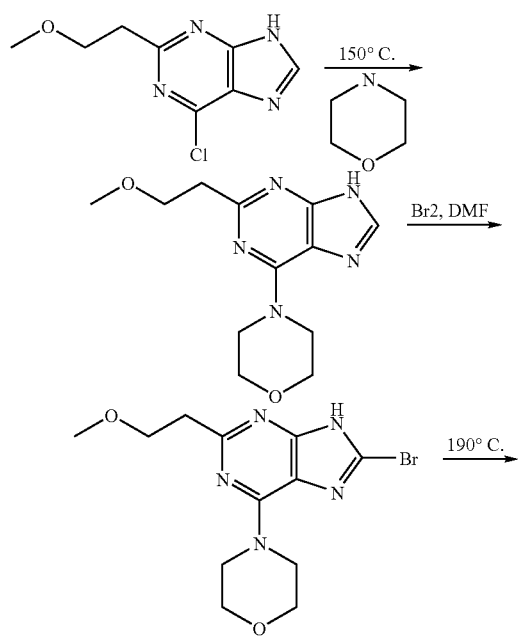

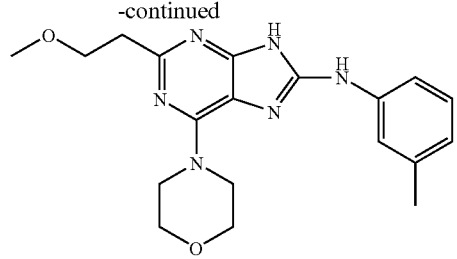

6-Chloro-2-(2-methoxy-ethyl)-9H-purine (0.5 g, 2.4 mmol, synthesized by following the procedure reported by Crespo and al.(*Journal of Medicinal Chemistry*, 1998, Vol. 41, No. 21, p. 4024) was heated in morpholine (1 mL, 5 eq) at 150° C. for 15 minutes. Reaction mixture was cooled to room temperature and distributed between dichloromethane and water. Organic layer was washed 2 times with water, then with brine, dried over MgSO$_4$ and 2-(2-methoxy-ethyl)6-morpholin-4-yl-9H-purine (0.46 g, 75%) was isolated by column chromatography.

ESMS calcd for C$_{12}$H$_{17}$N$_5$O$_2$: 263.14; Found: 286.2 (M+23)$^+$.

To a solution of 2-(2-methoxy-ethyl)-6-morpholin-4-yl-9H-purine (0.46 g, 1.7 mmol) in 1 mL of DMF bromine (0.34 g, 1.2 eq) was added dropwise, and a resulted solution was heated at 110° C. for 30 minutes. Solvent was removed in vacuo, a residue was dissolved in dichloromethane, washed with water, brine and dried over MgSO$_4$. Residue was purified by passing through silica gel (eluent dichloromethane:acetone:methanol 3:1:0.25) to afford 8-bromo-2-(2-methoxyethyl)-6-morpholin-4-yl-9H-purine (0.42 g, 70%).

ESMS calcd for C$_{12}$H$_{16}$BrN$_5$O$_2$: 341.05; Found: 342.0 (M+1)$^+$.

A suspension of 8-bromo-2-(2-methoxy-ethyl)-6-morpholin-4-yl-9H-purine (0.42 g, 1.2 mmol) in m-toluidine (0.5 mL, 3.8 eq) in a tightly stoppered flask was heated at 190° C. for 15 minutes. Column chromatography afforded [2-(2-methoxy-ethyl)-6-morpholin-4-yl-9H-purin-8-yl]-m-tolyl-amine (0.36 g, 81%) as an off-white solid.

$^1$H NMR (DMSO-d$_6$): δ 11.70 (s, 1H), 9.24 (s, 1H), 7.47 (s, 1H), 7.38 (d, J=8.4 Hz, 1H), 715 (t, J=7.6 Hz, 1H), 6.73 (d, J=7.5 Hz, 1H), 4.11 (m, 4H), 3.75 (t, J=6.9 Hz, 2H), 3.73 (m, 4H), 3.24 (s, 3H), 2.88 (t, J=6.9 Hz, 2H), 2.27 (s, 3H).

ESMS calcd for C$_{19}$H$_{24}$N$_6$O$_2$: 368.20; Found: 369.1 (M+1)$^+$.

EXAMPLE 53

Preparation of N$^2$,N$^8$-bis-(3-methylphenyl)-6-(4-methylpiperidinyl)-9H-purine-2,8-diamine

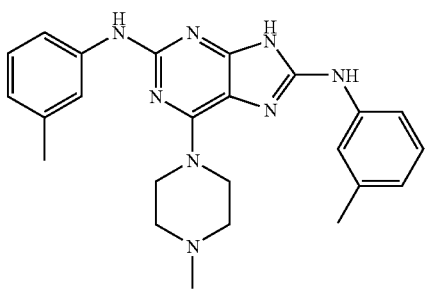

The title compound was prepared by a method as delineated herein.

$^1$H NMR (CD$_3$OD) δ (ppm), 7.4-7.1 (m, 6H), 6.77-6.82 (m, 2H), 4-3.5 (m, 11H), 2.30 (m, 6H).

ESMS calcd for C$_{24}$H$_{28}$N$_8$: 428.24; Found: 429.2 (M+H)$^+$.

EXAMPLE 54

Preparation of [2-(2-Benzyloxy-ethyl)-6-morpholin-4-yl-9H-purin-8-yl]-m-tolyl-amine

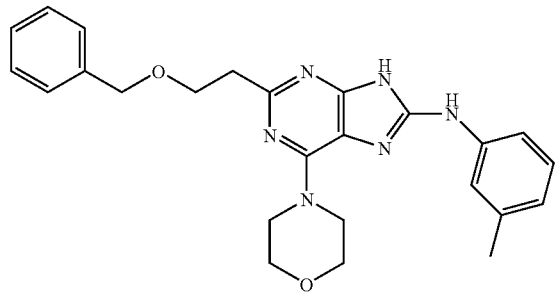

The title compound was prepared by a method as delineated herein.

$^1$H NMR (DMSO-d$_6$) δ (ppm), 11.70 (s, 1H), 9.24 (s, 1H), 7.47 (s, 1H), 7.36 (d, J=8.4 Hz, 1H), 7.32-7.26 (m, 5H), 7.14 (t, J=8.0 Hz, 1H), 6.72 (d, J=7.5 Hz, 1H), 4.49 (s, 2H), 4.10 (m, 4H), 3.86 (t, J=6.9 Hz, 2H), 3.71 (m, 4H), 2.94 (t, J=6.9 Hz, 2H), 2.27 (s, 3H).

ESMS calcd for C$_{25}$H$_{28}$N$_6$O$_2$: 444.23; Found: 445.3 (M+H)$^+$.

EXAMPLE 55

Preparation of 2-(6-Morpholin-4-yl-8-m-tolylamino-9H-purin-2-yl)-ethanol

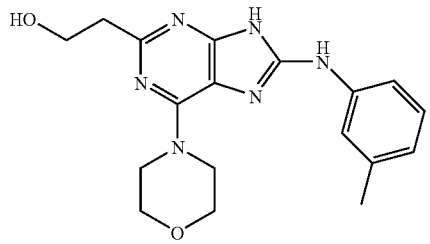

The title compound was prepared by a method as delineated herein.

$^1$H NMR (DMSO-dr) δ (ppm), 11.72 (s, 1H), 9.23 (s, 1H), 7.47 (s, 1H), 7.38 (d, J=7.6 Hz, 1H), 7.14 (t, J=7.2 Hz, 1H), 6.72 (d, J=6.0 Hz, 1H), 4.56 (s, 1H), 4.11 (m, 4H), 3.80 (m, 2H), 3.77 (m, 4H), 2.81 (m, 2H), 2.27 (s, 3H).

ESMS calcd for C$_{18}$H$_{22}$N$_6$O$_2$: 354.18; Found: 355.2 (M+H)$^+$.

EXAMPLE 56

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Phamacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of 5×10$^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test compound was dissolved in DMSO, and added to wells of the 96-well plate. The final DMSO concentration was adjusted to 0.25% in all cultures, including the compound-free control. Human TBP-1 cells were plated in wells, primed by adding IFNγ (100 U/mL) for 22 h and stimulated by adding SAC (0.025%) in the presence of different concentrations of the test compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with 1×10$^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of compounds delineated herein were tested on human PBMC or THP-1 cells. All of the test compounds are active. Unexpectedly, some of the test compounds have IC$_{50}$ values as low as <1 nM.

EXAMPLE 57

In Vivo Assays

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of compounds delineated herein reproducibly reduced the arthritic score and delayed the development of polyarthritis. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." The compounds of this invention had more than 50% reduction. A 30% or more reduction in colon-to-body weight ratio, relative to the vehicle treated control group, was considered significant.

Treatment of Qrohn's disease in $CD4^+CD45Rb^{high}$ T cell-reconstituted SCID colitis model mice: Spleen cells were prepared from normal female BALB/c mice. For cell purification, the following anti-mouse antibodies were used to label non-$CD4^+$ T cells: B220 (RA3-6B2), CD11b (M1/70), and $CD8\alpha$ (53-6.72). All antibodies were obtained from BioSource (Camarillo, Calif.). M450 anti-rat IgG-coated magnetic beads (Dynal, Oslo, Norway) were used to bind the antibodies and negative selection was accomplished using an MPC-1 magnetic concentrator. The enriched $CD4^+$ cells were then labeled for cell sorting with FITC-conjugated CD45RB (16A, Pharmingen, San Diego, Calif.) and PE-conjugated CD4 (CT-CD4, Caltag, Burlingame, Calif.). $CD4^+$ $CD45RB^{high}$ cells were operationally defined as the upper 40% of CD45Rb-staining $CD4^+$ cells and sorted under sterile conditions by flow cytometry. Harvested cells were resuspended at $4 \times 10^6$/mL in PBS and injected 100 μL intraperitoneally into female C.B-17 SCID mice. Compounds delineated herein and/or vehicle was orally administered once a day, 5 days per week, starting the day following the transfer. The transplanted SCID mice were weighed weekly and their clinical condition was monitored.

Colon tissue samples were fixed in 10% buffered formalin and embedded in paraffin. Sections (4 μm) collected from ascending, transverse, and descending colon were cut and stained with hematoxylin and eosin. The severity of colitis was determined based on histological examination of the distal colon sections, whereby the extent of colonic inflammation was graded on a scale of 0-3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue was digested further in RPMI containing 0.5 mg/mL collagenase D, 0.01 mg/mL DNase I (Boehringer Manheim), and antibiotics at 37° C. LP cells were then layered on a 40-100% Percoll gradient (Pharmacia, Uppsala, Sweden), and lymphocyte-enriched populations were isolated from the cells at the 40-100% interface.

To measure cytokine production, 48-well plates were coated with 10 μg/mL murine anti-CD3ε antibody (145-2C11) in carbonate buffer (PH 9.6) overnight at 4° C. $5 \times 10^5$ LP cells were then cultured in 0.5 ml of complete medium in precoated wells in the presence of 1 μg/mL soluble anti-CD28 antibody (37.51). Purified antibodies were obtained from Pharmingen. Culture supematants were removed after 48 h and assayed for cytokine production. Murine IFNγ was measured using an ELISA kit from Endogen (Cambridge, Mass.), according to the manufacturer's instructions.

Histological analysis showed that oral administration of compounds delineated herein reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous a compound described in the specification also can be made, screened for their inhibiting IL-12 activities, and used to practice this invention. Thus, other embodiments are also within the claims.

What is claimed is:

1. A compound of formula (I):

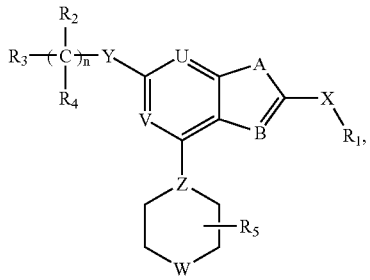

wherein $R_1$ is aryl or heteroaryl;

each of $R_2$ and $R_4$, independently, is H, halogen, CN, alkyl, $OR^a$, or $NR^aR^b$;

$R_3$ is H, halogen, CN, alkyl, alkenyl, alkynyl, aryl, heteroaryl, cyclyl, heterocyclyl, $OR^a$, $OC(O)R^a$, $OC(O)NR^aR^b$, $NR^aR^b$, $NR^aC(O)R^b$, $NR^aS(O)R^b$, $NR^aS(O)_2R^b$, $NR^aC(O)NR^bR^c$, $NR^aC(S)NR^bR^c$, $NR^aC(NR^b)NR^cR^d$, $NR^aC(O)OR^b$, $S(O)NR^aR^b$, $S(O)_2NR^aR^b$, $S(O)R^a$, $S(O)_2R^a$, $C(O)R^a$, $C(O)OR^a$, or $C(O)NR^aR^b$;

$R_5$ is H or alkyl;

n is 0, 1, 2, 3, 4, 5, or 6;

A is $NR^e$;

B is N;

X is O, S, S(O), $S(O)_2$, $NR^e$, or C(O);

Y is a covalent bond, C(O), C=$NR^a$, O, S, S(O), $S(O)_2$, or $NR^e$;

Z is N or CH;

each of U and V, independently, is CR; and

W is O, S, or $NR^e$;

in which each of $R^a$, $R^b$, $R^c$, and $R^d$, independently, is H, alkyl, aryl, heteroaryl, cyclyl, or heterocyclyl; $R^e$ is H, alkyl, aryl, acyl, or sulfonyl; and $R^f$ is H, alkyl, aryl, acyl, sulfonyl, alkoxyl, amino, ester, amide, CN, or halogen.

2. The compound of claim 1, wherein Z is N.

3. The compound of claim 2, wherein W is O.

4. The compound of claim 1, wherein X is $NR^e$.

5. The compound of claim 1, wherein $R_3$ is halogen, CN, alkyl, aryl, heteroaryl, $OR^a$, $OC(O)R^a$, $NR^aNR^b$, $NR^aC(O)R^b$, $C(O)OR^a$, or $C(O)NR^aR^b$.

6. The compound of claim 5, wherein $R_3$ is aryl, heteroaryl, aryloxyl, or heteroaryloxy.

7. The compound of claim 6, wherein $R_3$ is heteroaryl.

8. The compound of claim 6, wherein $R_3$ is pyridinyl, triazolyl, tetrazolyl, pyrimidinyl, thiazolyl, indolyl, or indolizinyl.

9. The compound of claim 6, wherein the compound is a N-oxide.

10. The compound of claim 1, wherein $R_1$ is aryl.

11. The compound of claim 10, wherein Y is $NR^e$.

12. The compound of claim 10, wherein Y is O.

13. The compound of claim 10, wherein $R_1$ is

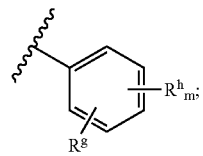

in which $R^9$ is H, halogen, CN, alkyl, or alkoxyl; $R^h$ is halogen, CN, hydroxyl, amino, alkyl, aryl, heteroaryl, alkoxyl, aryloxyl, heteroaryloxy, acyl, alkoxycarbonyl, alkylcarbonyl, mono- and dialkylaminocarbonyl, amidinyl, ureayl, guanadinyl, sulfonyl, or sulfonamidyl; and m is 0, 1, 2, 3, or 4.

14. The compound of claim 13, wherein $R_1$ is

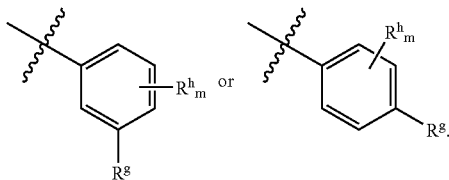

15. The compound of claim 13, wherein $R^9$ is H, F, Cl, Br, I, CN, Me, Et, Pr, i-Pr, OMe, or OEt.

16. The compound of claim 1, wherein the compound is

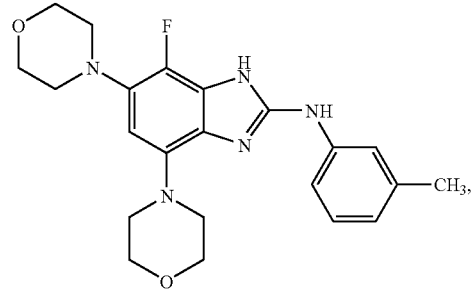

17. A method for treating an interleukin-12 overproduction-related disorder, selected from the group consisting of rheumatoid arthritis, sepsis, Crohn's disease, multiple sclerosis, psoriasis, and insulin-dependent diabetes mellitus, comprising administering to a subject in need thereof an effective amount of the compound of formula (I):

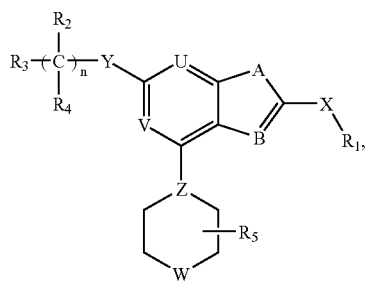

wherein $R_1$ is aryl or heteroaryl;

each of $R_2$ and $R_4$, independently, is H, halogen, CN, alkyl, $OR^a$, or $NR^aR^b$;

R$_3$ is H, halogen, CN, alkyl, alkenyl, alkynyl, aryl, heteroaryl, cyclyl, heterocyclyl, OR$^a$, OC(O)R$^a$, OC(O)NR$^a$R$^b$, NR$^a$R$^b$, NR$^a$C(O) R$^b$, NR$^a$S(O)R$^b$, NR$^a$S(O)$_2$R$^b$, NR$^a$C(O)NR$^b$R$^c$, NR$^a$C(S)NR$^b$R$^c$, NR$^a$C(NR$^b$)NR$^c$R$^d$, NR$^a$C(O)OR$^b$, S(O)NR$^a$R$^b$, S(O)$_2$NR$^a$R$^b$, S(O)R$^a$, S(O)$_2$R$^a$, C(O)R$^a$, C(O)OR$^a$, or C(O)NR$^a$R$^b$;

R$_5$ is H or alkyl;

n is 0, 1, 2, 3, 4, 5, or 6;

A is NR$^e$;

B is CR$^f$;

X is O, S, S(O), S(O)$_2$, NR$^e$, or C(O);

Y is a covalent bond, C(O), C=NR$^a$, O, S, S(O), S(O)$_2$, or NR$^e$;

Z is N or CH;

each of U and V, independently, is CR; and

W is O, S, or NR$^e$;

in which each of R$^a$, R$^b$, R$^c$, and R$^d$, independently, is H, alkyl, aryl, heteroaryl, cyclyl, or heterocyclyl; R$^e$ is H, alkyl, aryl, acyl, or sulfonyl; and R$^f$ is H, alkyl, aryl, acyl, sulfonyl, alkoxyl, amino, ester, amide, CN, or halogen.

18. The method of claim 17, wherein Z is N.

19. The method of claim 18, wherein W is O.

20. The method of claim 17, wherein X is NR$^e$.

21. The method of claim 17, wherein the compound is

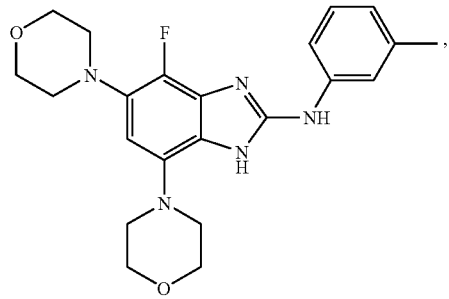

* * * * *